United States Patent
Siems et al.

(10) Patent No.: US 10,808,004 B2
(45) Date of Patent: Oct. 20, 2020

(54) TRITERPENE-GLYCOSIDE AS SWEETENER OR SWEETENER ENHANCER

(71) Applicant: Analyticon Discovery GmbH, Potsdam (DE)

(72) Inventors: Karsten Siems, Michendorf (DE); Grit Kluge, Trebbin (DE); Sven Jakupovic, Berlin (DE); Gregor Hetterling, Berlin (DE); Fotini Tschirintzi, Berlin (DE)

(73) Assignee: Analyticon Discovery GmbH, Potsdam (DE)

( * ) Notice: Subject to any disclaimer, the term of this patent is extended or adjusted under 35 U.S.C. 154(b) by 0 days.

(21) Appl. No.: 16/576,990

(22) Filed: Sep. 20, 2019

(65) Prior Publication Data

US 2020/0017541 A1    Jan. 16, 2020

Related U.S. Application Data

(62) Division of application No. 15/101,189, filed as application No. PCT/EP2013/075724 on Dec. 5, 2013, now Pat. No. 10,472,385.

(51) Int. Cl.

| | | |
|---|---|---|
| A23L 27/30 | (2016.01) | |
| C07J 17/00 | (2006.01) | |
| A23L 27/00 | (2016.01) | |
| A23G 3/36 | (2006.01) | |
| A23G 4/06 | (2006.01) | |
| A23G 4/08 | (2006.01) | |
| A61K 8/60 | (2006.01) | |
| A61Q 11/00 | (2006.01) | |

(52) U.S. Cl.
CPC .............. *C07J 17/005* (2013.01); *A23G 3/36* (2013.01); *A23G 4/06* (2013.01); *A23G 4/08* (2013.01); *A23L 27/00* (2016.08); *A23L 27/30* (2016.08); *A23L 27/36* (2016.08); *A61K 8/602* (2013.01); *A61Q 11/00* (2013.01); *A23V 2002/00* (2013.01)

(58) Field of Classification Search
None
See application file for complete search history.

(56) References Cited

U.S. PATENT DOCUMENTS

| | | |
|---|---|---|
| 4,084,010 A | 4/1978 | Takemoto et al. |
| 2010/0272838 A1 | 10/2010 | Prendergast |
| 2011/0027413 A1 | 2/2011 | Jia et al. |
| 2012/0059071 A1* | 3/2012 | Markosyan .............. A61K 8/97 514/777 |

FOREIGN PATENT DOCUMENTS

| | | |
|---|---|---|
| JP | S57-86266 A | 5/1982 |
| WO | 2008/149253 A2 | 12/2008 |

OTHER PUBLICATIONS

CHEMBLINK page showing CAS REG ID 88901-36-4, 2019.

* cited by examiner

*Primary Examiner* — Traviss C McIntosh, III
(74) *Attorney, Agent, or Firm* — Dilworth & Barrese, LLP

(57) ABSTRACT

What claimed is a method of sweetening or enhancing sweetening effect of a composition that is administered orally to an individual by adding a specific triterpene glycoside obtained from *Momordica grosvenorii* (*Siraitia grosvenori*).

8 Claims, No Drawings

TRITERPENE-GLYCOSIDE AS SWEETENER OR SWEETENER ENHANCER

RELATED APPLICATION

The present represents a divisional application derived from U.S. patent application Ser. No. 15/101,189 filed Jun. 2, 2016.

FIELD OF INVENTION

The invention relates to novel triterpene-glycoside compounds, which are obtainable by the extraction of *Momordica grosvenorii* (*Siraitia grosvenori*) and its physiologically acceptable salts which are useful as a sweetener or sweetener enhancer in preparations and compositions, especially oral edible compositions.

STATE OF THE ART

Sweetness is one of the primary taste and cravings of both animals and humans. The universal use of naturally occurring and synthetic sweeteners to satisfy this natural craving has not been met without its accompanying physiological disadvantages, e.g. obesity, nutritional imbalance and dental decay. To overcome these unwanted disadvantages considerable research efforts and expenditures have been made to develop alternative compounds, e.g. as substitute for the naturally occurring sweeteners or synthetic sweeteners which have no food value and are free of caloric input. While these artificial sweeteners enjoyed a wide use, and fulfilled the requirements of a sweet taste with no food value, and could be used without providing calories or damaging teeth, they were frequently found to possess inherent disadvantages that prevented their use for their intended purpose, e.g. because of their toxicity (p-ethoxy-phenylurea) or chromosome damage and bladder trouble (sodium cyclamate). Thus, these sweeteners could not be safely recommended for use as a sweetener and are apparently unacceptable for consumption. Saccharin compounds are also commonly used as artificial sweeteners, since cyclamates have been come under governmental restrictions. Although saccharin compounds possess sweetness characteristics, they are undesirable as the sole sweetening agent in most food and beverage compositions because of the lingering bitter aftertaste perceived by most users. While saccharin and the cyclamates have been in common use as artificial sweetening agents for a number of years, there has been more recently discovered a series of new artificial sweeteners.

For example, Horowitz and Gentili, U.S. Pat. No. 3,087,821, teach the use of various dihydrochalcones having sugar substituents (dihydrochalcones glycosides) as sweetening agents. All sweet dihydrochalkones have a licorice like aftertaste and linger in the mouth for some time.

*Siraitia grosvenori* (Luo han guo), a member of the Cucurbitaceae family, is a plant native to some regions of southern Asia and China. The sweet taste of fruits of luo han guo mainly comes from triterpene glycosides generally known as mogrosides. There are a number of mogrosides identified in luo han guo but generally mogroside V (CAS No: 88901-36-4) has the highest concentration compared to others (Table 1). Mogrol glycosides have the same core molecule-mogrol or oxo-nnogrol and differ from each other by number and type of glycosidic residues bonded to mogrol or oxo-mogrol molecules (US 2012/0059071, Kasai et al. Agric. Biol. Chem. (1989), 3347-3349), Matsumoto et. al. Chem. Pharm. Bu. (1990) 2030-2032. Several mogrosides taste very sweet, often >100× sweeter than sucrose, including the major triterpen glycoside of *Siraitia grosvenori*, mogroside V, and its isomer isomogroside V (US2011/0027413), but all of them have a certain bitter aftertaste. Major mogrosides present in Luo han guo fruits are compiled in the following Table A.

TABLE A

| Mogrosides | | |
|---|---|---|
| Substance | Mol. Formula | Mol. Weight |
| Mogroside IIE | $C_{42}H_{72}O_{14}$ | 801.01 |
| Mogroside III | $C_{48}H_{82}O_{19}$ | 963.15 |
| Mogroside IV | $C_{54}H_{92}O_{24}$ | 1125.29 |
| Mogroside V | $C_{60}H_{102}O_{29}$ | 1287.43 |
| Mogroside VI | $C_{66}H_{112}O_{34}$ | 1449.58 |
| 11-oxo-Mogroside V | $C_{66}H_{100}O_{29}$ | 1285.42 |
| Siamenoside I | $C_{54}H_{92}O_{22}$ | 1125.29 |

Leaves of *Stevia rebaudiana* are well known for its sweet taste due to its content of sweet diterpene glycosides. One of the major sweet compounds from stevia, Rebaudioside A, is approved as natural sweetener in US (since 2008) and EU (since 2011). Apart from its sweet taste, all sweeteners from stevia have a slower onset and longer duration than that of sugar, and a bitter or licorice-like aftertaste at high concentrations (Lemus-Mondaca et al. Food Chemistry 132 (2012) 1121-1132).

Another example is Symrise AG, EP 2529633 A1, which relates to triterpenes and triterpene glycosides and/or physiologically acceptable salts thereof. The triterpenes are, preferably naturally occurring triterpenes and triterpene glycosides from *Mycetia balansae*, for generating a sweet impression in an orally consumable formulation or for reinforcing the sweet impression of an orally consumable formulation. These triterpene-glycosides differ in structure from the triterpenes claimed in the present invention.

Accordingly, it is a primary object of the present invention to provide novel sweetener compounds and its physiologically acceptable salts, which have a positive sweet benefit in food and oral compositions. In particular, the object was to provide sweetener compounds which are capable to provide sweetness to consumable compositions in a way, that the balance between the degree of sweetness and the amount which has to be administered to obtain a sweet effect is comparable low, to overcome the aforesaid disadvantages associated with the prior art sweetener. It is another object of the present invention to provide sweetener compounds without astringent or bitter-taste aftertaste. The sweetener compounds to be specified should be toxicologically safe, effective already at relatively low concentrations, well tolerated by the digestion, stable (in particular in normal cosmetic and/or pharmaceutical formulations), and easy to formulate and economical to produce.

BRIEF DESCRIPTION OF THE INVENTION

The subject of the invention relates to:
17-(5-(4,5-dihydroxy-3-(3,4,5-trihydroxy-6-(hydroxymethyl)tetrahydro-2H-pyran-2-yloxy)-6-((3,4,5-trihydroxy-6-(hydroxymethyl)tetrahydro-2H-pyran-2-yloxy) methyl)tetrahydro-2H-pyran-2-yloxy)-6-hydroxy-6-methylheptan-2-yl)-4,4,9,13,14-pentamethyl-3-(3,4,5-trihydroxy-6-(hydroxymethyl)tetrahydro-2H-pyran-2-yloxy)-3,4,7,8,9,10,12,13,14,15,16,17-dodecahydro-1H-cyclopenta[a]phenanthren-11(2H)-one (Compound L), following formula I:

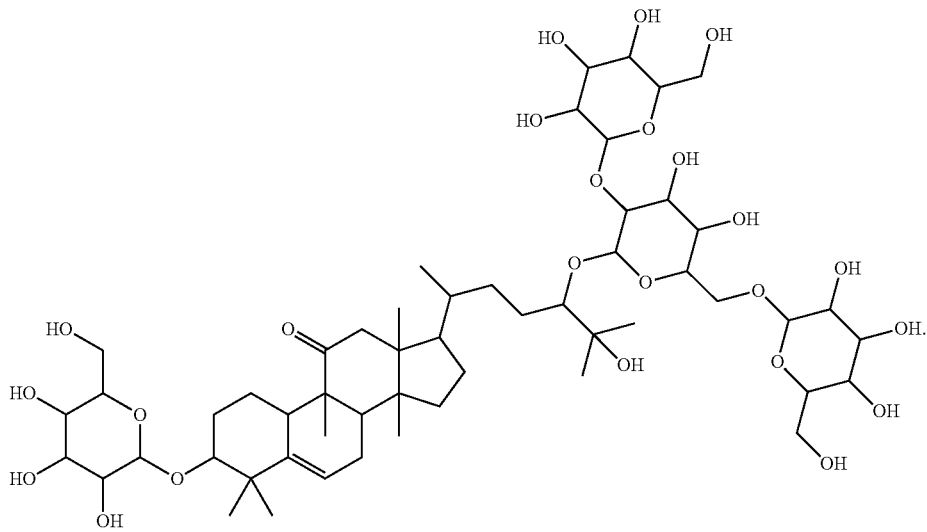

Particular preferred is:
(3S,9R,10R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-3-((2R,3R,4S,5S,6R)-3,4,5-trihydroxy-6-(hydroxymethyl)tetrahydro-2H-pyran-2-yloxy)-3,4,7,8,9,10,12,13,14,15,16,17-dodecahydro-1H-cyclopenta[a]phenanthren-11(2H)-one (Compound LI) following formula (II):

Surprisingly, it has been further observed that the sweetener compound of formula (I) has significantly less negative aftertaste at all and has high sweetening power.

Preparations

The present invention also relates to preparations, comprising the sweetener compound of formula (I) or (II). Such a preparation used to comprise further ingredients such as aroma compounds and/or flavoring agents and/or sweeteners and/or sweet-tasting substances.

Preferred aroma compounds, flavoring agents, sweeteners and sweet-tasting substances are described below in detailed.

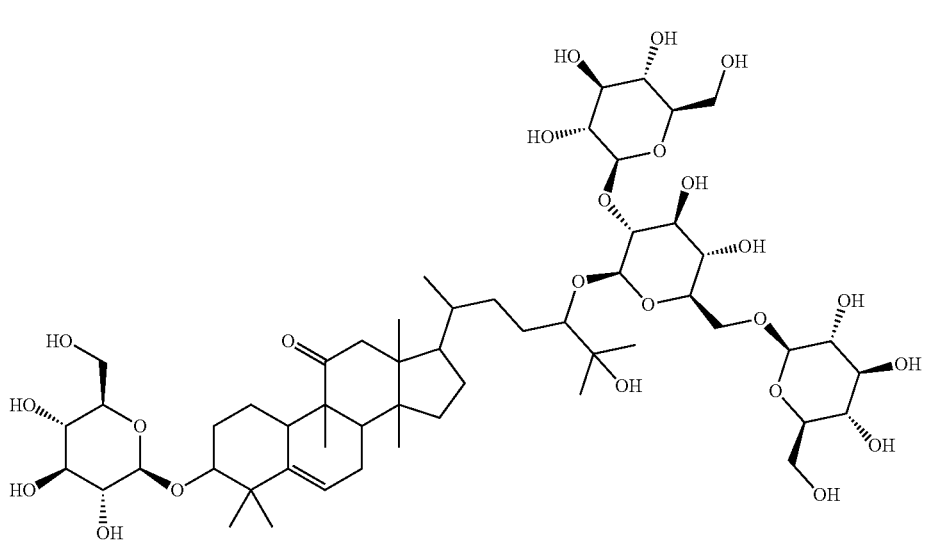

(II)

In the course of extensive studies on sweeteners, the present inventors succeeded in the isolation of a novel sweetener compound of formula (I) and found that the sweetener compound of formula (I) shows astonishingly good and strong sweetness when compared with that of sucrose and mogroside V.

The preparation of the present invention comprising at least one sweetener compound of formula (I) and can be used to impart a desirable sweetness and/or flavor to a variety of oral and food compositions and pharmaceutical compositions, such as beverages, edible foodstuff, dentifrices, lipsticks and the like, which may or may not be ingestible, with or without the use of other flavorants and sweeteners. The present invention also relates to a variety of oral and food compositions and the like embodying at least one compound of formula (I) as sweetener and/or flavoring agent.

The sweetener of this invention finds application in the wide range of edible substances generally, primarily in food compositions such as candies, confections and processed foods, and beverages such as beer and soft drinks. It is also well suited for imparting a sweet flavor to other edible substances such as medicines, toothpaste, adhesives for stamps and envelopes, animal feeds and baits and the like. These examples are given solely for illustration and it is not wished to limit the scope of this invention to sweetening any particular type or types of edible materials. As a general rule, the present sweetener may be used in any application where a sweet taste is desired. The present sweetener may be used alone or in combination with other sweeteners, nutritive or nonnutritive. Also, if desired, binders or diluents may be added to the sweetener. This is not usually necessary, however, as the sweetener is a solid having excellent handling properties. This makes mixing the sweetener with an edible substance a simple conventional operation. The sweetener may be mixed with the edible substance as a solid or as a solution, if desired.

The inventions further refers to the use of a sweetener compound of formula (I) to sweet or enhance the sweetening effect in compositions or preparations which are administered to an individual in an effective amount sufficient to produce the desired degree of sweetness.

Thus the invention further relates to a method for providing a sweetening effect and/or an enhanced sweetening effect in compositions, comprising administering to an individual a sweetener compound of formula (I) in an effective amount sufficient to produce the desired degree of sweetness.

The effective amount is preferably from 1 ppm to 2000 ppm, based on the total weight of the composition and the total sum of all compound of formula (I).

The food, oral and pharmaceutical compositions will be further described in detailed.

Food Compositions

Food compositions according to the invention are any preparations or compositions which are suitable for consumption and are used for nutrition or enjoyment purposes, and are generally products which are intended to be introduced into the human or animal oral cavity, to remain there for a certain time and then either be eaten (e.g. ready-to-eat foodstuffs or feeds, see also herein below) or removed from the oral cavity again (e.g. chewing gums). Such products include any substances or products which in the processed, partially processed or unprocessed state are to be ingested by humans or animals. They also include substances which are added to orally consumable products during their manufacture, preparation or treatment and which are intended to be introduced into the human or animal oral cavity.

The food compositions according to the invention also include substances which in the unchanged, treated or prepared state are to be swallowed by a human or animal and then digested; in this respect, the orally consumable products according to the invention also include casings, coatings or other encapsulations which are to be swallowed at the same time or which may be expected to be swallowed. The expression "orally consumable product" covers ready-to-eat foodstuffs and feeds, that is to say foodstuffs or feeds that are already complete in terms of the substances that are important for the taste. The expressions "ready-to-eat foodstuff" and "ready-to-eat feed" also include drinks as well as solid or semisolid ready-to-eat foodstuffs or feeds. Examples which may be mentioned are frozen products, which must be thawed and heated to eating temperature before they are eaten. Products such as yoghurt or ice-cream as well as chewing gums or hard caramels are also included among the ready-to-eat foodstuffs or feeds.

Preferred food compositions according to the invention also include "semi-finished products". Within the context of the present text, a semi-finished product is to be understood as being an orally consumable product which, because of a very high content of flavorings and taste-imparting substances, is unsuitable for use as a ready-to-eat orally consumable product (in particular foodstuff or feed). Only by mixing with at least one further constituent (e.g. by reducing the concentration of the flavorings and taste-imparting substances in question) and optionally further process steps (e.g. heating, freezing) is the semi-finished product converted into a ready-to-eat orally consumable product (in particular foodstuff or feed). Examples of semi-finished products which may be mentioned here are Food composition according to the invention preferably comprises one or more preparations for nutrition or enjoyment purposes. These include in particular (reduced-calorie) baked goods (e.g. bread, dry biscuits, cakes, other baked articles), confectionery (e.g. chocolates, chocolate bars, other products in bar form, fruit gums, dragées, hard and soft caramels, chewing gum), non-alcoholic drinks (e.g. cocoa, coffee, green tea, black tea, (green, black) tea drinks enriched with (green, black) tea extracts, rooibos tea, other herbal teas, fruit-containing soft drinks, isotonic drinks, refreshing drinks, nectars, fruit and vegetable juices, fruit or vegetable juice preparations), instant drinks (e.g. instant cocoa drinks, instant tea drinks, instant coffee drinks), meat products (e.g. ham, fresh sausage or raw sausage preparations, spiced or marinated fresh or salt meat products), eggs or egg products (dried egg, egg white, egg yolk), cereal products (e.g. breakfast cereals, muesli bars, precooked ready-to-eat rice products), dairy products (e.g. full-fat or reduced-fat or fat-free milk drinks, rice pudding, yoghurt, kefir, cream cheese, soft cheese, hard cheese, dried milk powder, whey, butter, buttermilk, partially or completely hydrolysed milk-protein-containing products), products made from soy protein or other soybean fractions (e.g. soy milk and products produced therefrom, drinks containing isolated or enzymatically treated soy protein, drinks containing soy flour, preparations containing soy lecithin, fermented products such as tofu or tempeh or products produced therefrom and mixtures with fruit preparations and optionally flavors), fruit preparations (e.g. jams, sorbets, fruit sauces, fruit fillings), vegetable preparations (e.g. ketchup, sauces, dried vegetables, frozen vegetables, precooked vegetables, boiled-down vegetables), snacks (e.g. baked or fried potato crisps or potato dough products, maize- or groundnut-based extrudates), fat- and oil-based products or emulsions thereof (e.g. mayonnaise, remoulade, dressings, in each case full-fat or reduced-fat), other ready-made dishes and soups (e.g. dried soups, instant soups, precooked soups), spices, spice mixtures and in particular seasonings which are used, for example, in the snacks field, sweetener preparations, tablets or sachets, other preparations for sweetening or whitening drinks or other foods. The preparations within the scope of the invention can also be used in the form of semi-finished products for the production of further preparations for nutrition or enjoyment purposes. The preparations within the scope of the invention can also be in the form of capsules, tablets (uncoated and coated tablets, e.g.

enteric coatings), dragées, granules, pellets, solids mixtures, dispersions in liquid phases, in the form of emulsions, in the form of powders, in the form of solutions, in the form of pastes, or in the form of other preparations which can be swallowed or chewed, and in the form of food supplements.

The preparations can also be in the form of capsules, tablets (uncoated and coated tablets, e.g. enteric coatings), dragées, granules, pellets, solids mixtures, dispersions in liquid phases, in the form of emulsions, in the form of powders, in the form of solutions, in the form of pastes, or in the form of other preparations which can be swallowed or chewed, for example in the form of food supplements.

The semi-finished products are generally used for the production of ready-to-use or ready-to-eat preparations for nutrition or enjoyment purposes.

Further constituents of a ready-to-eat preparation or semi-finished product for nutrition or enjoyment purposes can be conventional base substances, auxiliary substances and additives for foods or enjoyment foods, for example water, mixtures of fresh or processed, vegetable or animal base or raw substances (e.g. raw, roast, dried, fermented, smoked and/or boiled meat, bone, cartilage, fish, vegetables, herbs, nuts, vegetable juices, vegetable pastes or mixtures thereof), digestible or non-digestible carbohydrates (e.g. sucrose, maltose, fructose, glucose, dextrins, amylose, amylopectin, inulin, xylans, cellulose, tagatose), sugar alcohols (e.g. sorbitol, erythritol), natural or hardened fats (e.g. tallow, lard, palm fat, cocoa fat, hardened vegetable fat), oils (e.g. sunflower oil, groundnut oil, maize germ oil, olive oil, fish oil, soya oil, sesame oil), fatty acids or their salts (e.g. potassium stearate), proteinogenic or non-proteinogenic amino acids and related compounds (e.g. γ-aminobutyric acid, taurine), peptides (e.g. glutathione), natural or processed proteins (e.g. gelatin), enzymes (e.g. peptidases), nucleic acids, nucleotides, taste correctors for unpleasant taste impressions, further taste modulators for further, generally not unpleasant taste impressions, other taste-modulating substances (e.g. inositol phosphate, nucleotides such as guanosine monophosphate, adenosine monophosphate or other substances such as sodium glutamate or 2-phenoxypropionic acid), emulsifiers (e.g. lecithins, diacylglycerols, gum arabic), stabilisers (e.g. carrageenan, alginate), preservatives (e.g. benzoic acid and its salts, sorbic acid and its salts), antioxidants (e.g. tocopherol, ascorbic acid), chelators (e.g. citric acid), organic or inorganic acidifying agents (e.g. acetic acid, phosphoric acid), additional bitter substances (e.g. quinine, caffeine, limonene, amarogentine, humulone, lupulone, catechols, tannins), substances that prevent enzymatic browning (e.g. sulfite, ascorbic acid), ethereal oils, plant extracts, natural or synthetic colourings or colouring pigments (e.g. carotinoids, flavonoids, anthocyans, chlorophyll and derivatives thereof), spices, trigeminally active substances or plant extracts containing such trigeminally active substances, synthetic, natural or nature-identical flavorings or odorants as well as odour correctors.

Food compositions according to the invention, for example those in the form of preparations or semi-finished products, preferably comprise a flavor composition in order to complete and refine the taste and/or odour. A preparation can comprise as constituents a solid carrier and a flavor composition. Suitable flavor compositions comprise, for example, synthetic, natural or nature-identical flavorings, odorants and taste-imparting substances, reaction flavorings, smoke flavorings or other flavor-giving preparations (e.g. protein (partial) hydrolysates, preferably protein (partial) hydrolysates having a high arginine content, barbecue flavorings, plant extracts, spices, spice preparations, vegetables and/or vegetable preparations) as well as suitable auxiliary substances and carriers. Particularly suitable here are the flavor compositions or constituents thereof which produce a roasted, meaty (in particular chicken, fish, seafood, beef, pork, lamb, mutton, goat), vegetable-like (in particular tomato, onion, garlic, celery, leek, mushroom, aubergine, seaweed), spicy (in particular black and white pepper, cardamom, nutmeg, pimento, mustard and mustard products), fried, yeast-like, boiled, fatty, salty and/or pungent flavor impression and accordingly can enhance the spicy impression. The flavor compositions generally comprise more than one of the mentioned ingredients.

The food compositions of the present invention are preferably selected from the group comprising
confectionery, preferably reduced-calorie or calorie-free confectionery, preferably selected from the group comprising muesli bar products, fruit gums, dragées, hard caramels and chewing gum,
non-alcoholic drinks, preferably selected from the group comprising green tea, black tea, (green, black) tea drinks enriched with (green, black) tea extracts, rooibos tea, other herbal teas, fruit-containing low-sugar or sugar-free soft drinks, isotonic drinks, nectars, fruit and vegetable juices, fruit and vegetable juice preparations,
instant drinks, preferably selected from the group comprising instant (green, black, rooibos, herbal) tea drinks,
cereal products, preferably selected from the group comprising low-sugar and sugar-free breakfast cereals and muesli bars,
dairy products, preferably selected from the group comprising reduced-fat and fat-free milk drinks, yoghurt, kefir, whey, buttermilk and ice-cream,
products made from soy protein or other soybean fractions, preferably selected from the group comprising soy milk, products produced from soy milk, drinks containing isolated or enzymatically treated soy protein, drinks containing soy flour, preparations containing soy lecithin, products produced from preparations containing soy lecithin and mixtures with fruit preparations and optionally flavors,
sweetener preparations, tablets and sachets,
sugar-free dragées,
ice-cream, with or without milk-based constituents, preferably sugar-free.

Aroma or Flavoring Compounds

Aroma compounds and flavoring agents are well known in the art can be added to the flavor compositions of the invention. These flavoring agents can be chosen from synthetic flavoring liquid and/or oils derived from plants leaves, flowers, fruits and so forth, and combinations thereof. Representative flavoring liquids include: artificial, natural or synthetic fruit flavors such as eucalyptus, lemon, orange, banana, grape, lime, apricot and grapefruit oils and fruit essences including apple, strawberry, cherry, orange, pineapple and so forth; bean and nut derived flavors such as coffee, cocoa, cola, peanut, almond and so forth; and root derived flavors such as licorice or ginger.

The flavoring agent is preferably selected from the group consisting of essential oils and extracts, tinctures and balsams, such as, for example, anisole, basil oil, bergamot oil, bitter almond oil, camphor oil, citronella oil, lemon oil; *Eucalyptus citriodora* oil, eucalyptus oil, fennel oil, grapefruit oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if the flavored composition according to the invention comprises at least one flavoring agent, preferably two, three, four, five, six, seven, eight or more flavoring agents chosen from the following group: menthol (preferably l-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, linnonene (preferably D-linnonene, optionally as a constituent of an essential oil), piperitone, trans-sabinene hydrate, menthofuran, caryophyllene, germacrene D, cinnamaldehyde, mint lactone, thymol, gamma-octalactone, gamma-nonalactone, gamma-decalactone, (1,3E,5Z)-undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

In particular preferred aroma or flavoring compounds encompass menthol, cineol, eugenol, thymol, cinnamic aldehyde, peppermint oil, spearmint oil, eucalyptus oil, thyme oil, cinnamon oil, clove oil, spruce needle oil, fennel oil, sage oil, aniseed oil, star anise oil, chamomile oil, and caraway oil, and their mixtures.

Sweeteners and Sweet Tasting Substances

The term "sweeteners" here denotes substances having a relative sweetening power of at least 25, based on the sweetening power of sucrose (which accordingly has a sweetening power of 1). Sweeteners to be used in an orally consumable product (in particular foodstuff, feed or medicament) according to the invention (a) are preferably non-cariogenic and/or have an energy content of not more than 5 kcal per gram of the orally consumable product.

Advantageous sweeteners in a preferred orally consumable product (in particular foodstuff, feed or medicament) according to the invention are selected from the following groups (al) and Naturally occurring sweeteners, preferably selected from the group comprising miraculin, monellin, mabinlin, thaumatin, curculin, brazzein, pentaidin, D-phenylalanine, D-tryptophan, and extracts or fractions obtained from natural sources, comprising those amino acids and/or proteins, and the physiologically acceptable salts of those amino acids and/or proteins, in particular the sodium, potassium, calcium or ammonium salts;

neohesperidin dihydrochalcone, naringin dihydrochalcone, stevioside, steviolbioside, rebaudiosides, in particular rebaudioside A, rebaudioside B, rebaudioside C, rebaudioside D, rebaudioside E, rebaudioside F, rebaudioside G, rebaudioside H, dulcosides and rubusoside, suavioside A, suavioside B, suavioside G, suavioside H, suavioside I, suavioside J, baiyunoside 1, baiyunoside 2, phlomisoside 1, phlomisoside 2, phlomisoside 3 and phlomisoside 4, abrusoside A, abrusoside B, abrusoside C, abrusoside D, cyclocaryoside A and cyclocaryoside I, osladin, polypodoside A, strogin 1, strogin 2, strogin 4, selligueain A, dihydroquercetin 3-acetate, perillartin, telosmoside A15, periandrin I-V, pterocaryosides, cyclocaryosides, mukuroziocides, transanethole, transcinnamaldehyde, bryosides, bryonosides, bryonodulcosides, carnosiflosides, scandenosides, gypenosides, trilobatin, phloridzin, dihydroflavanols, hematoxylin, cyanin, chlorogenic acid, albiziasaponin, telosmosides, gaudichaudioside, mogrosides, mogroside V, hernandulcins, monatin, phyllodulcin, glycyrrhetinic acid and derivatives thereof, in particular glycosides thereof such as glycyrrhizine, and the physiologically acceptable salts of those compounds, in particular the sodium, potassium, calcium or ammonium salts;

extracts or concentrated fractions of the extracts, selected from the group comprising thaumatococcus extracts (katamfe plant), extracts from *Stevia* ssp. (in particular *Stevia rebaudiana*), swingle extracts (*Momordica* or *Siratia grosvenorii*, Luo-Han-Guo), extracts from *Glycyrrhiza* ssp. (in particular *Glycyrrhiza glabra*), extracts from *Rubus* ssp. (in particular *Rubus suavissimus*), citrus extracts and extracts from *Lippia dulcis*;

Synthetic sweet-tasting substances, preferably selected from the group comprising magap, sodium cyclamate or other physiologically acceptable salts of cyclamic acid, acesulfame K or other physiologically acceptable salts of acesulfame, neohesperidin dihydrochalcone, naringin dihydrochalcone, saccharin, saccharin sodium salt, aspartame, superaspartame, neotame, alitame, advantame, perillartin, sucralose, lugduname, carrelame, sucrononate and sucrooctate.

Suitable sweet-tasting substances, including natural sources of these substances such as for example sweet-tasting carbohydrates or sugars (e.g. sucrose (synonymous with saccharose), trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrin) or vegetable preparations containing predominantly these carbohydrates (e.g. from sugar beet (*Beta vulgaris* ssp., sugar fractions, sugar syrup, molasses), from sugar cane (*Saccharum officinarum* ssp., e.g. molasses, sugar syrups), from sugar maple (*Acer* ssp.), from agave (agave thick juice), synthetic/enzymatic hydrolysates of starch or sucrose (e.g. invert sugar syrup, highly enriched fructose syrups made from corn starch), fruit concentrates (e.g. from apples or pears, apple syrup, pear syrup), sugar alcohols (e.g. erythritol, threitol, arabitol, ribitol, xylitol, sorbitol, mannitol, dulcitol, lactitol), proteins (e.g. miraculin, monellin, thaumatin, curculin, brazzein), artificial sweeteners (magap, sodiumcyclamate, acesulfame K, neohesperidin dihydrochalcone, saccharin sodium salt, Aspartame®, superaspartame, neotame, alitame, sucralose, lugduname, carrelame, sucrononate, sucrooctate, monatin), certain sweet-tasting amino acids (glycine, D-leucine, D-threonine, D-asparagine, D-phenylalanine, D-tryptophan, L-proline), other sweet-tasting low-molecular substances, e.g. rebaudioside, stevioside, mogrosides, hernandulcin, phyllodulcin, dihydrochalcone glycosides, glycyrrhizin, glycyrrhetinic acid ammonium salt or other glycyrrhetinic acid derivatives, extracts from sweet tasting plants, in particular *Momordica grosvenori* [Luo Han Guo] *Hydrangea macrophylla, Stevia* ssp. (e.g. *Stevia rebaudiana*), *Rubus suavissimus, Polypodium vulgare, Abrus precatorius, Pterocarya paliurus, Baccharis gaudichaudiana, Albizia myriophylla, Bryonia dioica, Phlomis betonicoides, Hemsleya carnosiflora, Lippia dulcis, Gynostemma pentaphyllum, Glycyrrhiza glabra* (liquorice) or individual sweet tasting, substances isolated from those plants.

Thickeners

Advantageous thickeners in a preferred orally consumable product (in particular foodstuff, feed or medicament) according to the invention are selected from the group comprising: crosslinked polyacrylic acids and derivatives thereof, polysaccharides and derivatives thereof, such as xanthan gum, agar-agar, alginates or tyloses, cellulose derivatives, for example carboxymethylcellulose or hydroxycarboxymethylcellulose, fatty alcohols, monoglycerides and fatty acids, polyvinyl alcohol and polyvinylpyrrolidone.

Preference is given according to the invention to an orally consumable product (in particular foodstuff or feed) which comprises milk thickened with lactic acid bacteria and/or cream thickened with lactic acid bacteria and which preferably is selected from the group comprising yoghurt, kefir and quark.

A food composition according to the invention comprising milk thickened with lactic acid bacteria and/or cream thickened with lactic acid bacteria is advantageously an orally consumable product which comprises a probiotic, wherein the probiotic is preferably selected from the group comprising *Bifidobacterium animalis* subsp. *lactis* BB-12, *Bifidobacterium animalis* subsp. *lactis* DN-173 010, *Bifidobacterium animalis* subsp. *lactis* HNO19, *Lactobacillus acidophilus* LA5, *Lactobacillus acidophilus* NCFM, *Lactobacillus johnsonii* La1, *Lactobacillus casei* immunitass/defensis, *Lactobacillus casei* Shirota (DSM 20312), *Lactobacillus casei* CRL431, *Lactobacillus reuteri* (ATCC 55730) and *Lactobacillus rhamnosus* (ATCC 53013).

Additives for Chewing Gums

Particular preference is given to an orally consumable product (in particular foodstuff, feed or medicament) according to the invention that is a chewing gum and comprises a chewing-gum base. The chewing-gum base is preferably selected from the group comprising chewing-gum or bubble-gum bases. The latter are softer, so that gum bubbles can also be formed therewith. Preferred chewing-gum bases according to the invention include, in addition to the natural resins or the natural latex chicle that are traditionally used, elastomers such as polyvinyl acetate (PVA), polyethylene, (low or medium molecular weight) polyisobutene (PIB), polybutadiene, isobutene-isoprene copolymers (butyl rubber), polyvinyethyl ether (PVE), polyvinylbutyl ether, copolymers of vinyl esters and vinyl ethers, styrene-butadiene copolymers (styrene-butadiene rubber, SBR) or vinyl elastomers, for example based on vinyl acetate/vinyl laurate, vinyl acetate/vinyl stearate or ethylene/vinyl acetate, as well as mixtures of the mentioned elastomers, as described, for example, in EP 0 242 325, U.S. Pat. Nos. 4,518,615, 5,093,136, 5,266,336, 5,601,858 or U.S. Pat. No. 6,986,709. In addition, chewing-gum bases that are preferably to be used according to the invention preferably comprise further constituents such as, for example, (mineral) fillers, plasticisers, emulsifiers, antioxidants, waxes, fats or fatty oils, such as, for example, hardened (hydrogenated) vegetable or animal fats, mono-, di- or tri-glycerides. Suitable (mineral) fillers are, for example, calcium carbonate, titanium dioxide, silicon dioxide, talcum, aluminium oxide, dicalcium phosphate, tricalcium phosphate, magnesium hydroxide and mixtures thereof. Suitable plasticisers, or agents for preventing adhesion (detackifiers), are, for example, lanolin, stearic acid, sodium stearate, ethyl acetate, diacetin (glycerol diacetate), triacetin (glycerol triacetate), triethyl citrate. Suitable waxes are, for example, paraffin waxes, candelilla wax, carnauba wax, microcrystalline waxes and polyethylene waxes. Suitable emulsifiers are, for example, phosphatides such as lecithin, mono- and di-glycerides of fatty acids, for example glycerol monostearate.

Chewing gums according to the invention (in particular as disclosed above) preferably comprise constituents such as sugars of different types, sugar substitutes, other sweet-tasting substances, sugar alcohols (in particular sorbitol, xylitol, mannitol), ingredients having a cooling effect, taste correctors for unpleasant taste impressions, further taste-modulating substances (e.g. inositol phosphate, nucleotides such as guanosine monophosphate, adenosine monophosphate or other substances such as sodium glutamate or 2-phenoxypropionic acid), humectants, thickeners, emulsifiers, stabilisers, odour correctors and flavors (e.g. *eucalyptus*-menthol, cherry, strawberry, grapefruit, vanilla, banana, citrus, peach, blackcurrant, tropical fruits, ginger, coffee, cinnamon, combinations (of the mentioned flavors) with mint flavors as well as spearmint and peppermint on their own). The combination inter alia of the flavors with further substances that have cooling, warming and/or mouth-watering properties is of particular interest.

Vitamins

In another embodiment of the present invention the compositions may include vitamins (component e1). Vitamins have diverse biochemical functions. Some have hormone-like functions as regulators of mineral metabolism (e.g., vitamin D), or regulators of cell and tissue growth and differentiation (e.g., some forms of vitamin A). Others function as antioxidants (e.g., vitamin E and sometimes vitamin C). The largest number of vitamins (e.g. B complex vitamins) act as precursors for enzyme cofactors, that help enzymes in their work as catalysts in metabolism. In this role, vitamins may be tightly bound to enzymes as part of prosthetic groups: For example, biotin is part of enzymes involved in making fatty acids. Vitamins may also be less tightly bound to enzyme catalysts as coenzymes, detachable molecules that function to carry chemical groups or electrons between molecules. For example, folic acid carries various forms of carbon group—methyl, formyl, and methylene—in the cell. Although these roles in assisting enzyme-substrate reactions are vitamins' best-known function, the other vitamin functions are equally important. In the course of the present invention suitable vitamins are selected from the group consisting of Vitamin A (retinol, retinal, beta carotene),
Vitamin $B_1$ (thiamine),
Vitamin $B_2$ (riboflavin),
Vitamin $B_3$ (niacin, niacinamide),
Vitamin $B_5$ (panthothenic acid),
Vitamin $B_6$ (pyridoxine, pyridoxamine, paridoxal), Vitamin $B_7$ (biotin),
Vitamin $B_9$ (folic acid, folinic acid),
Vitamin $B_{12}$ (cyanobalamin, hydoxycobalmin, methylcobalmin),
Vitamin C (ascorbic acid),
Vitamin D (cholecalciferol),
Vitamin E (tocopherols, tocotrienols), and
Vitamin K (phyolloquinone, menaquinone).

The preferred vitamins are ascorbic acid and tocopherols. Said vitamins may be present in the food composition in amounts of about 0.1 to about 5% b.w., and preferably about 0.5 to about 1% b.w.

Oral Compositions

Typical examples for non-food oral compositions encompass products for cleaning and protecting teeth and refreshing the oral cavity.

The oral compositions of the present invention typically comprise an abrasive system (abrasive or polishing agent), such as e.g. silicas, calcium carbonates, calcium phosphates, aluminium oxides and/or hydroxyapatites, surface-active substances, such as e.g. sodium lauryl sulfate, sodium lauryl sarcosinate and/or cocamidopropyl betaine, moisture-retaining agents, such as e.g. glycerol and/or sorbitol, thickening agents, such as e.g. carboxymethylcellulose, polyethylene glycols, carrageenan and/or Laponite®, sweeteners, such as e.g. saccharin, flavor correctants for unpleasant taste impressions, flavor correctants for further, as a rule not unpleasant taste impressions, flavor-modulating substances (e.g. inositol phosphate, nucleotides, such as guanosine monophosphate, adenosine monophosphate or other substances, such as sodium glutamate or 2-phenoxypropionic acid), cooling active compounds, such as e.g. menthol derivatives (e.g. L-menthyl lactate, L-menthyl alkyl carbonates, menthone ketals, menthanecarboxylic acid amides), 2,2,2-trialkylacetic acid amides (e.g. 2,2-diisopropylpropionic acid methylamide), icilin and icilin derivatives, stabilizers and active compounds, such as e.g. sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, chlorhexidine, cetylpyridinium chloride, aluminium lactate, potassium citrate, potassium nitrate, potassium chloride, strontium chloride, hydrogen peroxide, aromas, sodium bicarbonate and/or odour correctants.

Formulations or products according to the invention in the form of chewing gums or, in particular, dental care chewing gums comprise chewing gum bases which comprise elastomers, such as, for example, polyvinyl acetates (PVA), polyethylenes, (low or medium molecular weight) polyisobutenes (PIB), polybutadienes, isobutene-isoprene copolymers (butyl rubber), polyvinyl ethyl ethers (PVE), polyvinyl butyl ethers, copolymers of vinyl esters and vinyl ethers, styrene/butadiene copolymers (styrene/butadiene rubber, SBR) or vinyl elastomers, e.g. based on vinyl acetate/vinyl laurate, vinyl acetate/vinyl stearate or ethylene/vinyl acetate, and mixtures of the elastomers mentioned, as described, for example, in EP 0 242 325, U.S. Pat. No. 4,518,615, 5,093,136, 5,266,336 5,601,858 or 6,986,709. In addition, chewing gum bases comprise further constituents, such as, for example, sugars, sugar substitutes or sweet-tasing substances in particular those described in WO 2009/21558, (mineral) fillers, plasticizers, emulsifiers, antioxidants, waxes, fats or fatty oils, such as, for example, hardened (hydrogenated) plant or animal fats, and mono-, di- or tri-glycerides. Suitable (mineral) fillers are, for example, calcium carbonate, titanium dioxide, silicon dioxide, talc, aluminium oxide, dicalcium phosphate, tricalcium phosphate, magnesium hydroxide and mixtures thereof. Suitable plasticizers or agents for preventing sticking (detackifiers) are, for example, lanolin, stearic acid, sodium stearate, ethyl acetate, diacetin (glycerol diacetate), triacetin (glycerol triacetate) and triethyl citrate. Suitable waxes are, for example, paraffin waxes, candelilla wax, carnauba wax, microcrystalline waxes and polyethylene waxes. Suitable emulsifiers are, for example, phosphatides, such as lecithin, and monoand diglycerides of fatty acids, e.g. glycerol monostearate.

Formulations or products according to the invention (in particular those which are in the form of an oral care formulation or product or in the form of a formulation) preferably additionally comprise one or more aroma and/or flavoring substances, such as essential oils and extracts, tinctures and balsams, such as, for example, anisole, basil oil, bergamot oil, bitter almond oil, camphor oil, citronella oil, lemon oil; *Eucalyptus citriodora* oil, eucalyptus oil, fennel oil, grapefruit oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if said formulations or products comprise at least one aroma substance, preferably 2, 3, 4, 5, 6, 7, 8, 9, 10 or more aroma substances, chosen from the following group: menthol (preferably l-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, limonene (preferably D-limonene, optionally as a constituent of an essential oil), piperitone, trans-sabinene hydrate, menthofuran, caryophyllene, germacrene D, cinnamaldehyde, mint lactone, thymol, gamma-octalactone, gamma-nonalactone, gamma-decalactone, (1,3E,5Z)-undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

Pharmaceutical Compositions

Pharmaceutical compositions according to the present invention may include similar additives as already explained for the food and oral compositions, such as aroma and flavors. Pharmaceutical compositions may further include, oil bodies or emulsifiers and in particular co-actives supporting the beneficial properties of the pharmaceutical active agent. Therefore, the border between food compositions and pharmaceutical compositions is in flow and it should be understood that components cited for one application are recommended for the other mutatis-mutandis without literal repetition.

Methods
Further subject of the present invention is a method of sweetening or enhancing sweetening effect of a composition that is administered orally to an individual by adding the sweetener compound of formula (I)
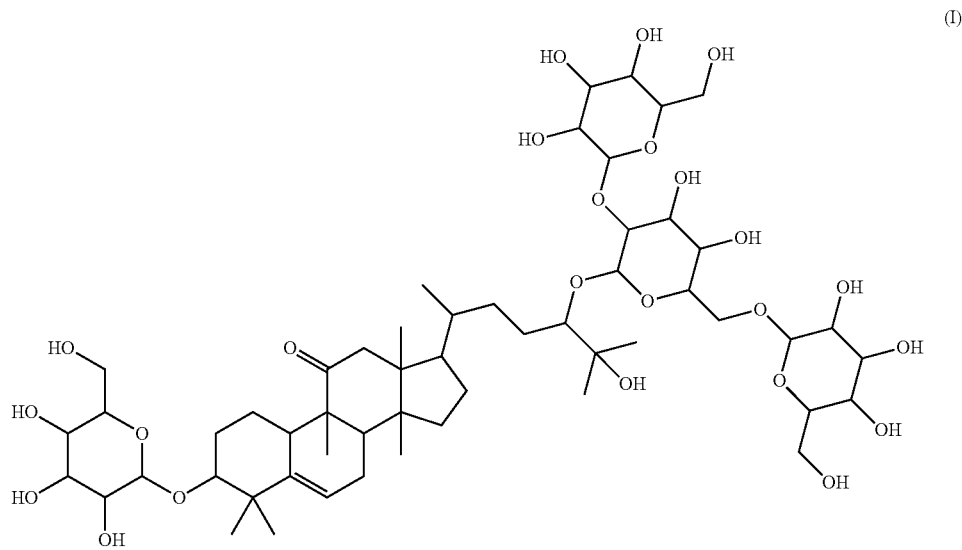
or formula (II) respectively
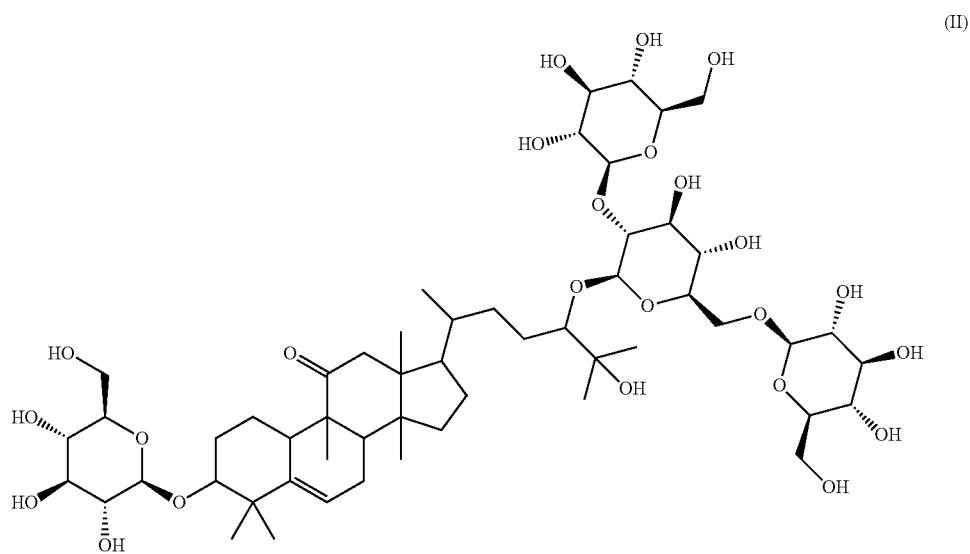

Preferably, the compound of formula (I) is used in an amount from 1 ppm to 2000 ppm by weight, based on the total weight of the. More preferably, the sweetener compound of formula (I) is used in an amount from 10 ppm to 1000 ppm by weight, most preferably in an amount of 20 ppm to 500 ppm by weight, based on the total weight of the composition.

Extracts

Further subject of the invention is an extract containing 17-(5-(4,5-dihydroxy-3-(3,4,5-trihydroxy-6-(hydroxymethyl)tetrahydro-2H-pyran-2-yloxy)-6-((3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-3-(3,4,5-trihydroxy-6-(hydroxymethyl)tetrahydro-2H-pyran-2-yloxy)-3,4,7,8,9,10,12,13,14,15,16,17-dodecahydro-1H-cyclopenta[a]phenanthren-11(2H)-one (Compound L)

according to formula I:

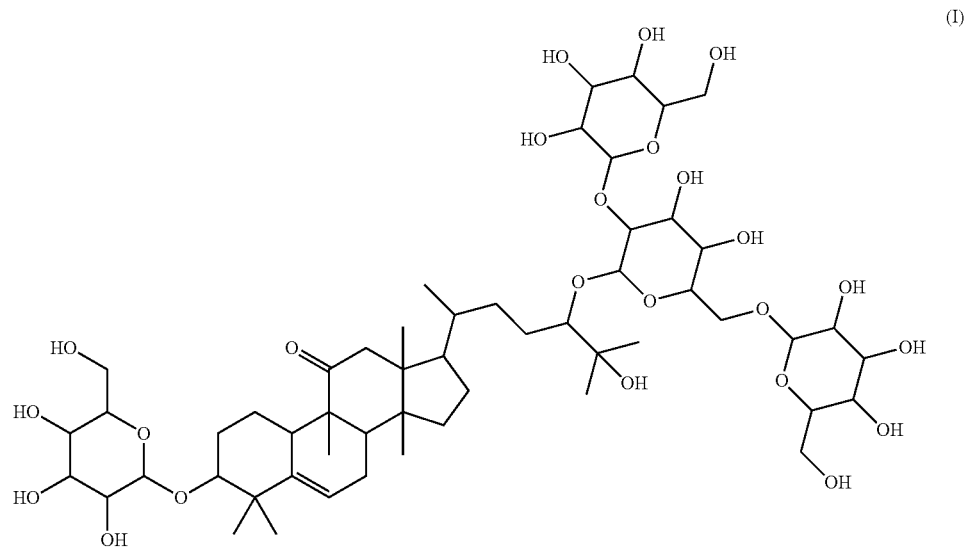

or formula (II) respectively

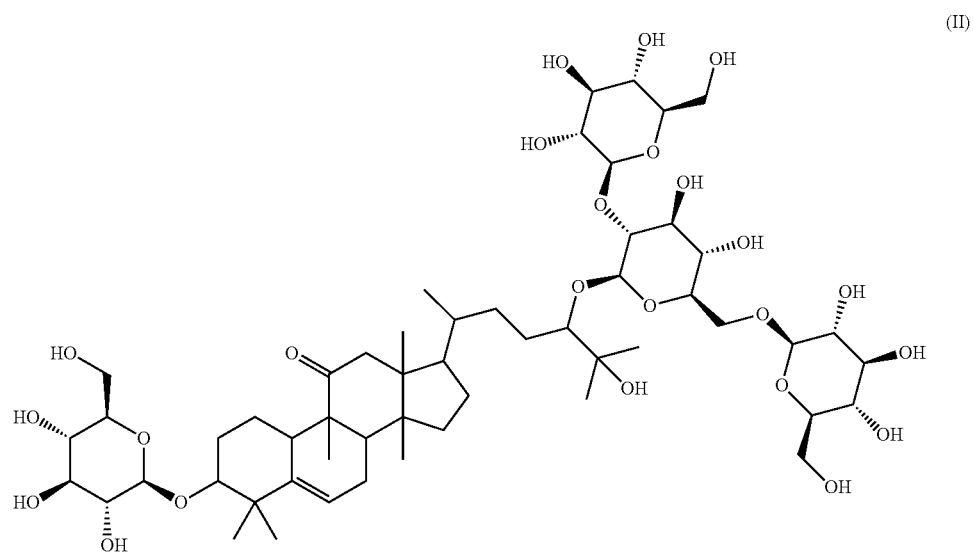

wherein the extract is obtainable by the method of aqueous and/or alcoholic extraction of plant materials selected from the group consisting of *Momordica grosvenorii* (*Siraitia grosvenori*).

In this context "plant materials" refers to parts of the respective plant of *Momordica* grosvenorii (*Siraitia grosvenori*). The plant materials may include parts of the whole plant selected from the group consisting of blossoms, fruits, buds, roots, seeds and/or leaves or the whole plant itself.
Extraction The extracts according to the present invention may be prepared by methods known per se, i.e. for example by aqueous, alcoholic or aqueous/alcoholic extraction of the plants or parts thereof or shells of the litchi fruits. Suitable extraction processes are any conventional extraction processes, such as maceration, re-maceration, digestion, agitation maceration, vortex extraction, ultrasonic extraction, counter current extraction, percolation, re percolation, evacolation (extraction under reduced pressure), diacolation and solid/liquid extraction under continuous reflux. Percolation is advantageous for industrial use. Litchi shells are preferably used as the starting material and may be mechanically size-reduced before the extraction process. Any size reduction methods known to the expert, for example freeze grinding, may be used. Preferred solvents for the extraction process are organic solvents, water (preferably hot water with a temperature above 80° C. and more particularly above 95° C. or mixtures of organic solvents and water, more particularly low molecular weight alcohols with more or less high water contents. Extraction with methanol, ethanol, isopropanol and water-containing mixtures thereof is particularly preferred. The extraction process is generally carried out at about 20 to about 100° C. and preferably at about 50 to about 70° C. In one preferred embodiment, the extraction process is carried out in an inert gas atmosphere to avoid oxidation of the ingredients of the extract. This is particularly important where extraction is carried out at temperatures above 40° C. The extraction times are selected by the expert in dependence upon the starting material, the extraction process, the extraction temperature and the ratio of solvent to raw material, etc. After the extraction process, the crude extracts obtained may optionally be subjected to other typical steps, such as for example purification, concentration and/or decoloration. If desired, the extracts thus prepared may be subjected, for example, to the selective removal of individual unwanted ingredients. The extraction process may be carried out to any degree, but is usually continued to exhaustion. Typical yields (=extract dry matter, based on the quantity of raw material used) in the extraction of the starting materials are of the order of about 1 to about 20, %, preferably about 2 to about 15 and more preferably about 5 to about 10% b.w.—calculated on the starting materials.

The content in the extract of compound (L) differs from batch to batch depending on the used raw material of fruits of *M. grosvenori*. Usually the major triterpene glycoside in extracts of *M. grosvenori* is Mogroside V (CAS 88901-36-4) with a relative amount of 50 to 90% of the total amount of triterpene glycosides. Compound (L) is usually present in amounts ranging from 0.01 to 5% of total amount of triterpene glycosides in *M. grosvenori*.

INDUSTRIAL APPLICATION

More particularly, the present invention also refers to an oral edible composition, comprising an edible substance and at least one compound of formula (I)

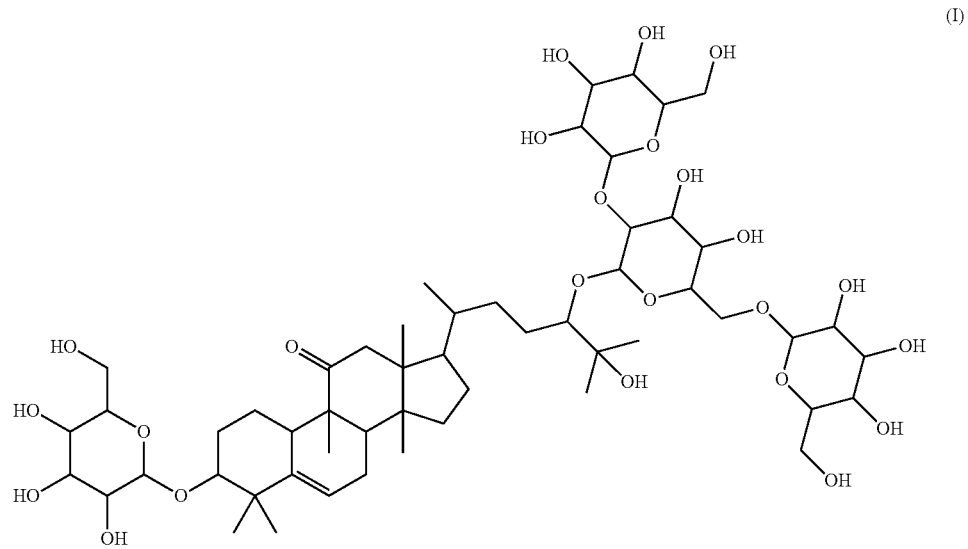

or formula (II) respectively

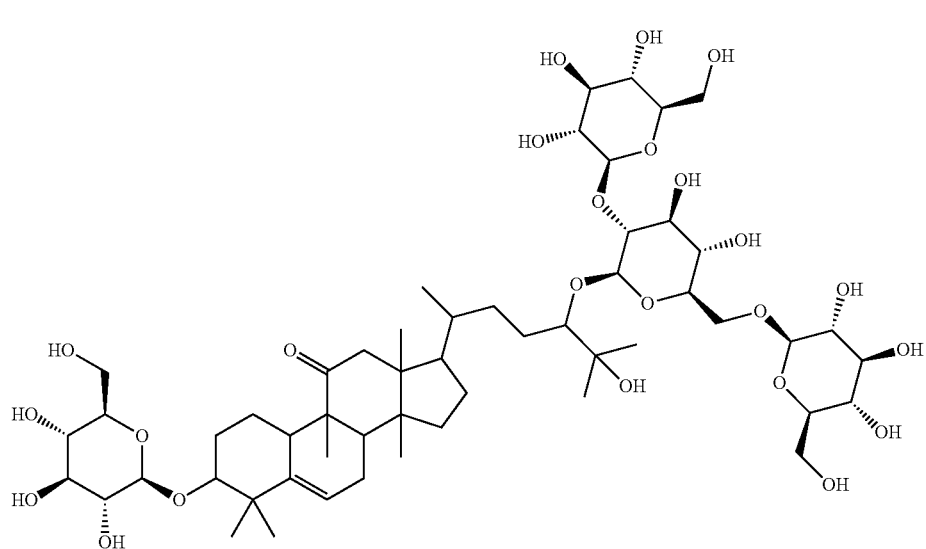

(II)

in an effective amount sufficient to produce the desired degree of sweetness.

The effective amount is preferably from 1 ppm to 2000 ppm (basis edible substance), more preferably from 10 ppm by weight to 1000 ppm by weight, most preferred from 20 ppm by weight to 500 ppm by weight, and calculated on the total weight of the composition.

Preferred edible compositions are the preferred food compositions which have been described herein.

Further, the compounds of formula (I) or (II) respectively are suitable as sweetener in liable compositions.

The invention will be further described by the following Examples. These Examples are provided to illustrate the invention and are not to be construed as limiting the scope of the invention.

EXAMPLES

The examples which follow are intended to illustrate the present invention without limiting the invention. Unless indicated otherwise all amounts, parts and percentages are based on the weight and the total amount or on the total weight and the total amount of the preparations.

Example 1

Extraction and Identification of Compounds of Formula (I)
A) Extraction 2 kg dried fruits of *Momordica grosvenori* (Syn. *Siraitia grosvenori*), provided by Cfm Oskar Tropitzsch, Marktredwitz, Germany, were extracted with 18l methanol-MTB-ether at room temperature for 24 h (yield: 275 g extract). 1 kg dried fruits of *Momordica grosvenori* (Syn. *Siraitia grosvenori*), provided by DAXINGANLING SNOW LOTUS HERB BIO-TECHNOLOGY CO., LTD., China, were extracted with 10l methanol at room temperature for 24 h (yield: 310 g extract).
B) Enrichment In order to remove very polar sugars the raw extract were dissolved in 5l water-methanol (9:1) and 500 ml of absorber resin HP-20 was added. The filtered resin was washed with water to elute the polar ingredients which are not wanted. Elution with methanol yielded 37 g of a mixture of triterpene-glycosides.

C) Pre-Fractionation by Normal Phase Chromatography

The resulted fraction of B) was then separated by medium pressure chromatography under the following conditions:
stationary phase: Silica 60 (Merck)
mobile phase solvent A: $CHCl_3$-methanol-water 1680:720:120
mobile phase solvent: B $CHCl_3$-methanol-water 1350:900:225
gradient: 100% A to 50% A in 40 min, 10 min 50% A, 10 min 90% methanol-10% water
column dimension: 50×250 mm Seven fractions were collected and evaporated as set out in the following Table C:

TABLE C

| Fraction | Fractions Volume [ml] | Yield [g] |
|---|---|---|
| C-1780-A | 150 | 5.85 |
| C-1780-B | 220 | 4.72 |
| C-1780-C | 450 | 3.85 |
| C-1780-D | 550 | 2.96 |
| C-1780-E | 410 | 2.08 |
| C-1780-F | 500 | 2.32 |
| C-1780-G | 550 | 13.38 |

D) Pre-Fractionation by Reverse Phase Chromatography 300 g raw extract of *M. grosvenori* were separated by reverse phase medium pressure chromatography under the following conditions:

Conditions of the separation of enriched triterpene glycoside fraction:
stationary phase: RP-18, 40-63u (Merck)
mobile phase solvent A: water
mobile phase solvent B: methanol
column dimension: 50×250 mm Seven Fractions were collected as set out in the following Table D:

TABLE D

| Fraction | Volume [ml] | Yield [g] |
| --- | --- | --- |
| H-1714-B | 3000 | 54.06 |
| H-1714-C | 3000 | 32.52 |
| H-1714-D | 3000 | 36.69 |
| H-1714-E | 3000 | 36.87 |
| H-1714-F | 3000 | 11.25 |
| H-1714-G | 3000 | 3.57 |
| H-1714-I | 3000 | 0.96 |

E) Final Purification by Reverse Phase Chromatography

Pure compounds were isolated by reverse phase chromatography using enriched fractions generated by pre-fractionation steps described in step D).

TABLE 1

Conditions of the separation of C-1780-C

| | |
| --- | --- |
| stationary phase | LichrospherSelect B. 10 µm |
| mobile phase solvent A | water + 5 mM ammoniumformiat + 0.1% formic acid |
| mobile phase solvent B | acetonitril/methanol = 1:1 + 5 mM ammoniumformiat + 0.1% formic acid |
| flowrate | 80 ml/min |
| gradient | 36-65% B in 57 min |
| detection | ELSD and UV |
| column dimension | 50 × 250 mm |
| used prefraction sample | 3.85 g C-1780-C |

TABLE 2

Conditions of the separation of C-1780-D

| | |
| --- | --- |
| stationary phase | LichrospherSelect B. 10 µm |
| mobile phase solvent A | water + 5 mM ammoniumformiat + 0.1% formic acid |
| mobile phase solvent B | acetonitril/methanol = 1:1 + 5 mM ammoniumformiat + 0.1% formic acid |
| flowrate | 80 ml/min |
| gradient | 32-50% B in 57 min |
| detection | ELSD and UV |
| column dimension | 50 × 250 mm |
| used prefraction sample | 2.96 g C-1780-D |

TABLE 3

Conditions of the separation of C-1780-E

| | |
| --- | --- |
| stationary phase | LichrospherSelect B. 10 µm |
| mobile phase solvent A | water + 5 mM ammonium formiate + 0.1% formic acid |
| mobile phase solvent B | acetonitrile/methanol = 1:1 + 5 mM ammonium formiate + 0.1% formic acid |
| flowrate | 80 ml/min |
| gradient | 32-50% B in 57 min |
| detection | ELSD and UV |
| column dimension | 50 × 250 mm |
| used pre-fraction sample | 2.08 g C-1780-E |

TABLE 4

Conditions of the separation of C-1780-F

| | |
| --- | --- |
| stationary phase | LichrospherSelect B. 10 µm |
| mobile phase solvent A | water + 5 mM ammonium formiate + 0.1% formic acid |
| mobile phase solvent B | acetonitrile/methanol = 1:1 + 5 mM ammonium formiate + 0.1% formic acid |
| flowrate | 80 ml/min |
| gradient | 29-49% B in 57 min |
| detection | ELSD and UV |
| column dimension | 50 × 250 mm |
| used pre-fraction sample | 2.32 g C-1780-F |

TABLE 5

Conditions of the separation of H-1949-G

| | |
| --- | --- |
| stationary phase | LichrospherSelect B. 10 µm |
| mobile phase solvent A | water + 5 mM ammonium formiate + 0.1% formic acid |
| mobile phase solvent B | acetonitrile/methanol = 1:1 + 5 mM ammonium formiate + 0.1% formic acid |
| flowrate | 80 ml/min |
| gradient | 35-50% B in 57 min |
| detection | ELSD and UV |
| column dimension | 50 × 250 mm |
| used pre-fraction sample | 0.57 g H-1714-G |

TABLE 6

Conditions of the separation of C-1750-N

| | |
| --- | --- |
| stationary phase | Kromasil C-18 |
| mobile phase solvent A | water + 0.1% formic acid |
| mobile phase solvent B | acetonitrile + 0.1% formic acid |
| flowrate | 80 ml/min |
| gradient | 20-37% B in 57 min |
| detection | ELSD and UV |
| column dimension | 50 × 250 mm |
| used pre-fraction sample | 1.3 g H-1714-F |

TABLE 7

Conditions of the separation of C-1743-A

| | |
| --- | --- |
| stationary phase | Kromasil C-18 |
| mobile phase solvent A | water + 5 mM ammonium formiate + 0.1% formic acid |
| mobile phase solvent B | methanol = 1:1 + 5 mM ammonium formiate + 0.1% formic acid |
| flowrate | 80 ml/min |
| gradient | 53-62% B in 57 min |
| detection | ELSD and UV |
| column dimension | 50 × 250 mm |
| used pre-fraction sample | 2.08 g H-1714-F |

TABLE 8

Conditions of the separation of H-1714-G

| | |
| --- | --- |
| stationary phase | Kromasil C-18 |
| mobile phase solvent A | water + 0.1% formic acid |
| mobile phase solvent B | acetonitrile + 0.1% formic acid |
| flowrate | 80 ml/min |
| gradient | 20-37% B in 57 min |
| detection | ELSD and UV |
| column dimension | 50 × 250 mm |
| used prefraction sample | 1.3 g H-1714-F |

F) Analytical Characterization of Isolated Triterpene-Glycosides

Fractions from preparative HPLC were collected (40 ml each) and analyzed by HPLC-MS. Fractions containing the same compound according to retention time and mass spectrum were combined, evaporated and analyzed by HPLC-MS and NMR ($^1$H-NMR; HH-COSY; HSQC; HMBC). Structures were elucidated by interpretation of NMR and MS data.

TABLE 9

Conditions of the HPLC-MS of isolated compounds

| | |
|---|---|
| HPLC | HPLC PE series 200 |
| MS System | Applied Biosystems API 150. 165 or 365 |
| Data system | Analyst 1.3 |
| stationary phase | Phenomenex Luna C8 (2). 5 μm. 50 × 4.6 mm |
| flowrate | 1.2 mL/min |
| detection | (+/(−)-ESI. Fast-Switching-mode. ELSD (Sedex 75) |
| injection volume | 10 μL |
| mobile phase: | A: 5 mM ammonium formiate and 0.1% formic acid |
| | B: Acetonitril/Methanol = 1:1 + 5 mM ammonium formiate + 0.1% formic acid (pH 3) |

TABLE 9-continued

Conditions of the HPLC-MS of isolated compounds

| gradient | time [min] | % A | % B |
|---|---|---|---|
| | 0 | 95 | 5 |
| | 6 | 0 | 100 |
| | 8 | 0 | 100 |

G) Identification: Analytical Characterization of the Compounds

The isolated compounds of formula (I) are characterized through mass spectroscopy and NMR spectroscopy. The compounds were identified as:

| Compounds | Structure and IUPAC name |
|---|---|
| Compounds Aa | 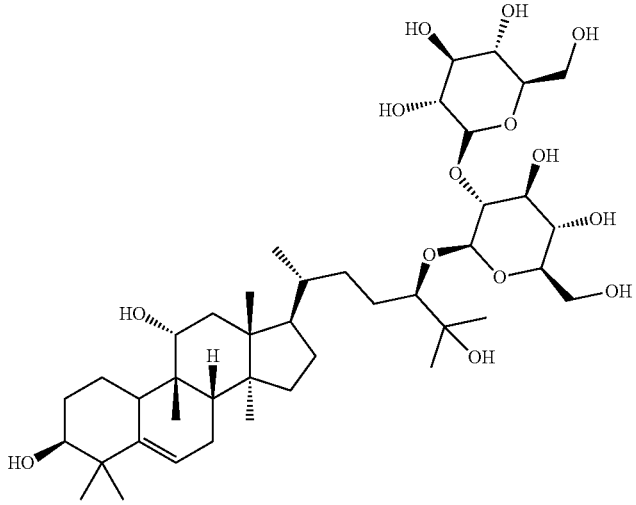<br>(2S,3R,4S,5S,6R)-2-((2S,3R,4S,5S,6R)-2-((3R,6R)-6-((3S,8S,9R,11R,13R,14S,17R)-3,11-dihydroxy-4,4,9,13,14-pentamethyl-2,3,4,7,8,9,10,11,12,13,14,15,16,17-tetradecahydro-1H-cyclopenta[a]phenanthren-17-yl)-2-hydroxy-2-methylheptan-3-yloxy)-4,5-dihydroxy-6-(hydroxymethyl)tetrahydro-2H-pyran-3-yloxy)-6-(hydroxymethyl)tetrahydro-2H-pyran-3,4,5-triol |
| Compound Bb | 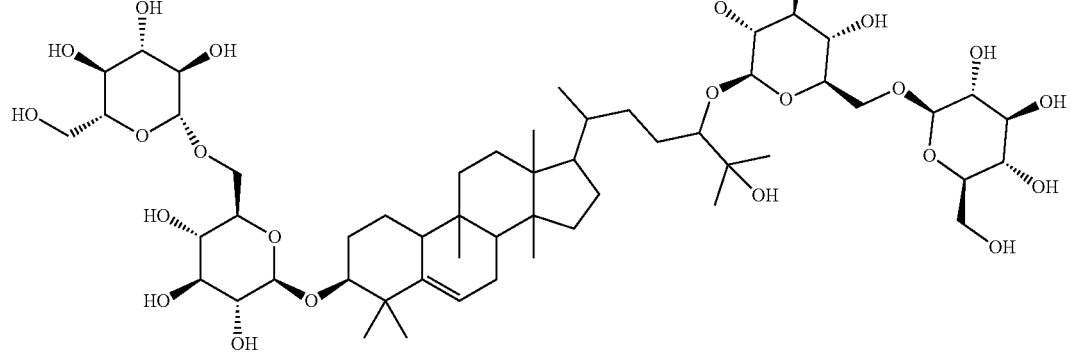<br>(2S,3R,4S,5S,6R)-2-((2S,3R,4S,5S,6R)-4,5-dihydroxy-2-((3R,6R)-2-hydroxy-2-methyl-6-((3S,9R,13R,14S,17R)-4,4,9,13,14-pentamethyl-3-((2R,3R,4S,5S,6R)-3,4,5-trihydroxy-6-(((2R,3R,4S,5S,6R)-3,4,5-trihydroxy-6- |

| Compounds | Structure and IUPAC name |
|---|---|
| | (hydroxymethyl)tetrahydro-2H-pyran-2-yloxy)methyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol |
| Compound Cc | 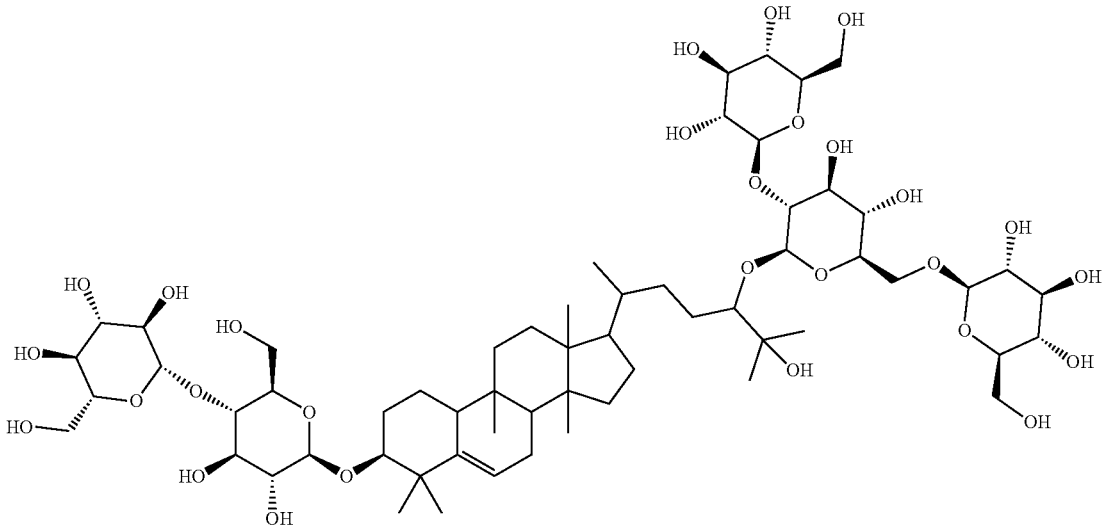<br>(2S,3R,4S,5S,6R)-2-((2R,3S,4R,5R,6R)-6-((3S,9R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-2,3,4,7,8,9,10,11,12,13,14,15,16,17-tetradecohydro-1H-cyclopenta[a]phenanthren-3-yloxy)-4,5-dihydroxy-2-(hydroxymethyl)tetrahydro-2H-pyran-3-yloxy)-6-(hydroxymethyl)tetrahydro-2H-pyran-3,4,5-triol |
| Compound Dd | (2S,3R,4S,5S,6R)-2-((2R,3R,4S,5S,6R)-2-((3S,8R,9R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5- |

| Compounds | Structure and IUPAC name |
|---|---|
| | trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-2,3,4,7,8,9,10,11,12,13,14,15,16,17-tetradecahydro-1H-cyclopenta[a]phenanthren-3-yloxy)-4,5-dihydroxy-6-(hydroxymethyl)tetrahydro-2H-pyran-3-yloxy)-6-(hydroxymethyl)tetrahydro-2H-pyran-3,4,5-triol |
| Compound Ee | 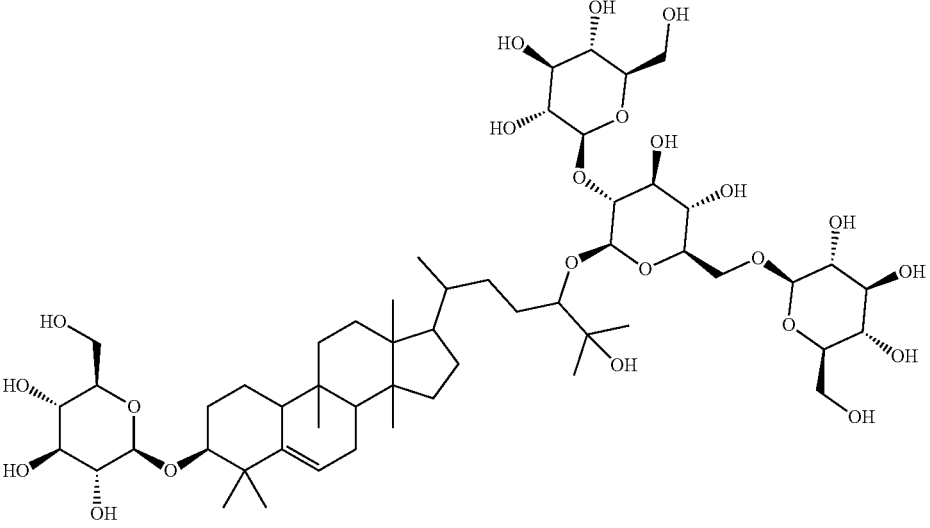<br>(2S,3R,4S,5S,6R)-2-((2S,3R,4S,5S,6R)-4,5-dihydroxy-2-((3R,6R)-2-hydroxy-2-methyl-6-((3S,8R,9R,13R,14S,17R)-4,4,9,13,14-pentamethyl-3-((2R,3R,4S,5S,6R)-3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol |
| Compound Ff | 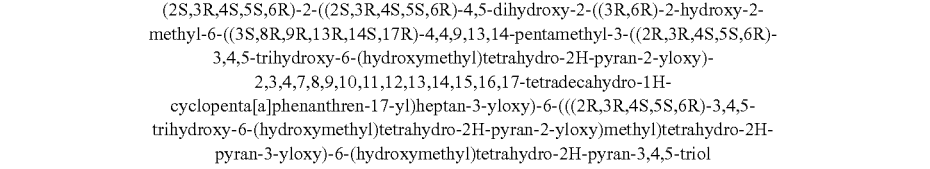<br>(2S,3R,4S,5S,6R)-2-((2R,3R,4S,5S,6R)-2-((3S,8S,9R,11R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5- |

| Compounds | Structure and IUPAC name |
|---|---|
| | trihydroxy-6-(hydroxymethyl)tetrahydro-2H-pyran-2-yloxy)methyl)tetrahydro-2H-pyran-2-yloxy)-6-hydroxy-6-methylheptan-2-yl)-11-hydroxy-4,4,9,13,14-pentamethyl-2,3,4,7,8,9,10,11,12,13,14,15,16,17-tetradecahydro-1H-cyclopenta[a]phenanthren-3-yloxy)-4,5-dihydroxy-6-(hydroxymethyl)tetrahydro-2H-pyran-3-yloxy)-6-(hydroxymethyl)tetrahydro-2H-pyran-3,4,5-triol |
| Compound Gg | 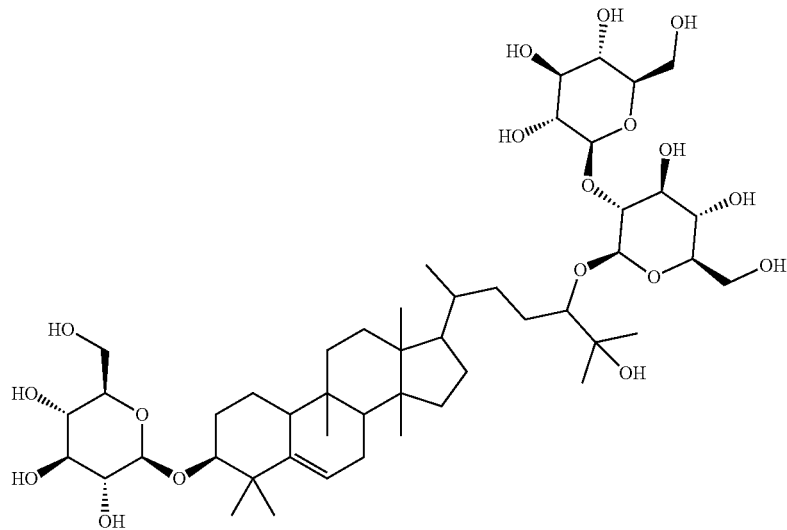<br>(2S,3R,4S,5S,6R)-2-((2S,3R,4S,5S,6S)-4,5-dihydroxy-2-((3R,6R)-2-hydroxy-2-methyl-6-((3S,9R,13R,14S,17R)-4,4,9,13,14-pentamethyl-3-((2R,3R,4S,5S,6R)-3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-(hydroxymethyl)tetrahydro-2H-pyran-3-yloxy)-6-(hydroxymethyl)tetrahydro-2H-pyran-3,4,5-triol |
| Compound Hh | 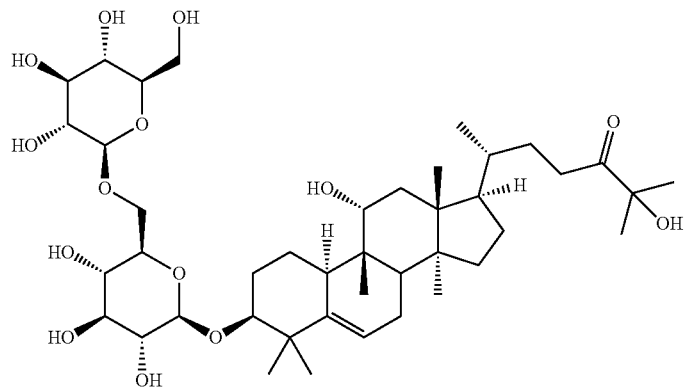<br>(6R)-2-hydroxy-6-((3S,9R,10R,11R,13R,14S,17R)-11-hydroxy-4,4,9,13,14-pentamethyl-3-((2R,3R,4S,5S,6R)-3,4,5-trihydroxy-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-2,3,4,7,8,9,10,11,12,13,14,15,16,17-tetradecahydro-1H-cyclopenta[a]phenanthren-17-yl)-2-methylheptan-3-one |

| Compounds | Structure and IUPAC name |
|---|---|
| Compound Jj | 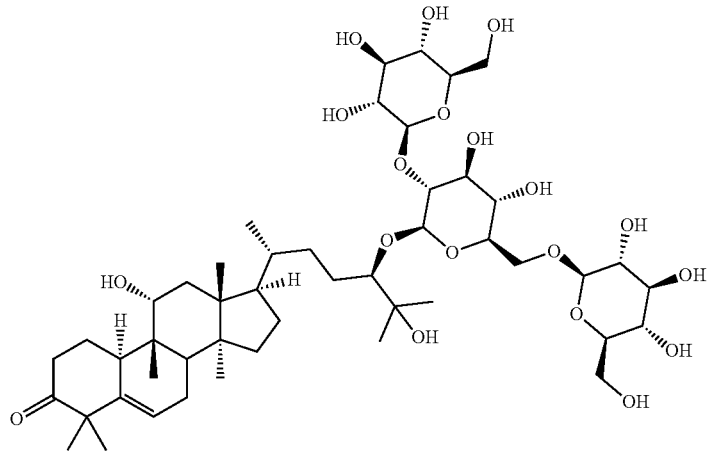<br>(9R,10R,11R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-11-hydroxy-4,4,9,13,14-pentamethyl-4,7,8,9,10,11,12,13,14,15,16,17-dodecahydro-1H-cyclopenta[a]phenanthren-3(2H)-one |
| Compound Kk | 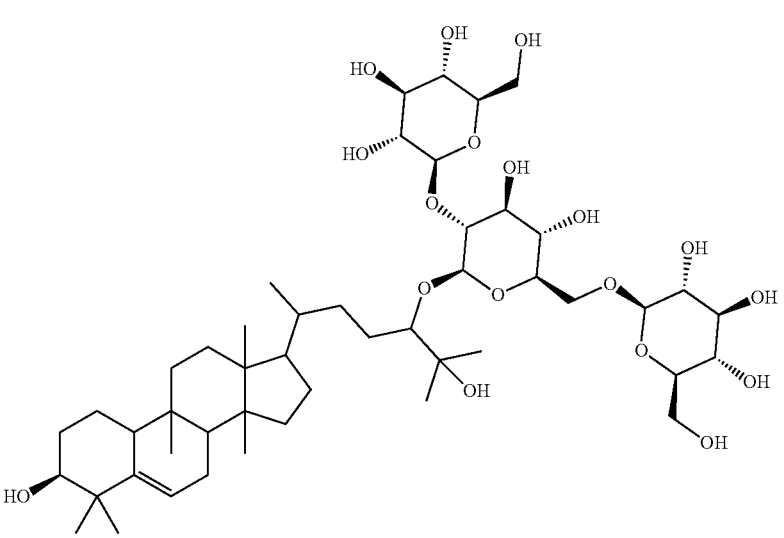<br>(2S,3R,4S,5S,6R)-2-((2S,3R,4S,5S,6R)-4,5-dihydroxy-2-((3R,6R)-2-hydroxy-6-((3S,9R,10S,13R,14S,17R)-3-hydroxy-4,4,9,13,14-pentamethyl-2,3,4,7,8,9,10,11,12,13,14,15,16,17-tetradecahydro-1H-cyclopenta[a]phenanthren-17-yl)-2-methylheptan-3-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol |

| Compounds | Structure and IUPAC name |
|---|---|
| Compound Ll | 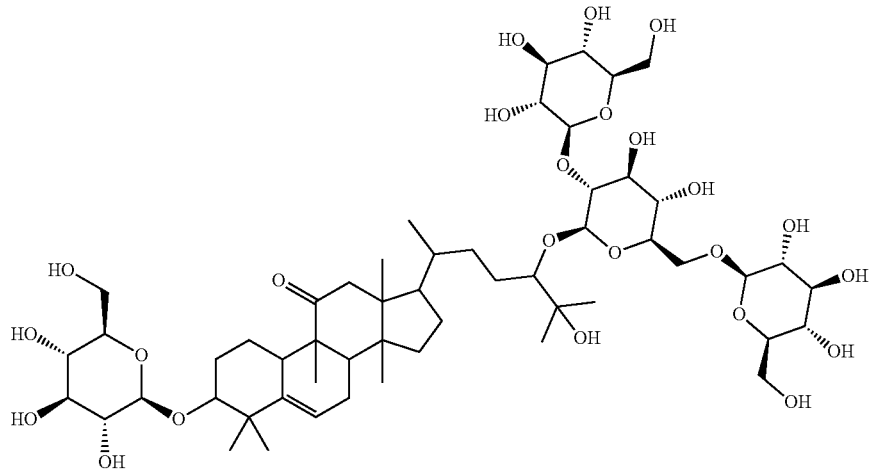<br>(3S,9R,10R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-3-((2R,3R,4S,5S,6R)-3,4,5-trihydroxy-6-(hydroxymethyl)tetrahydro-2H-pyran-2-yloxy)-3,4,7,8,9,10,12,13,14,15,16,17-dodecahydro-1H-cyclopenta[a]phenanthren-11(2H)-one |
| Compound Mm | 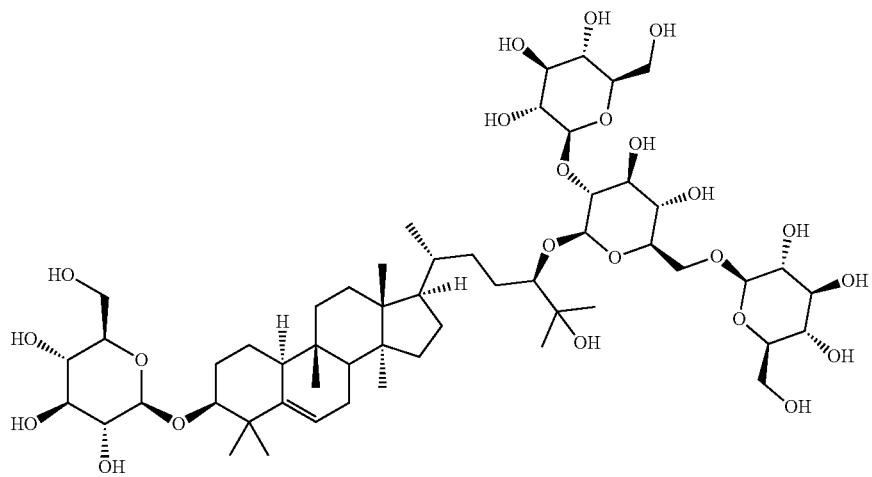<br>(2S,3R,4S,5S,6R)-2-((2S,3R,4S,5S,6R)-4,5-dihydroxy-2-((3R,6R)-2-hydroxy-2-methyl-6-((3S,9R,10S,13R,14S,17R)-4,4,9,13,14-pentamethyl-3-((2R,3R,4S,5S,6R)-3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol. |

For the avoidance of doubt it should be noted that when adding the extract as described above for sweetening of a composition or sweetness enhancement, Component Ll is added along with all other components mentioned above.

Example 2

Organoleptic Test of Compound L Against Sucrose and Mogroside V

The isolated Compound Ll according to formula (II) was dissolved in non-carbonated mineral water ("Fonsana Quelle") in a concentration of 0.4 mg/ml (400 ppm). The sweet taste of the samples was compared by a panel of 4 panelists with a solution of sucrose in a concentration of 20 mg/ml and with a solution of the known sweetener mogroside V (isolated by AnalytiCon from *Momordica grosvenori*) in a concentration of 0.1 mg/ml (100 ppm).

The sweetness was evaluated as follows:

3=sweeter than the control solution

2=sweetness comparable with the control solution

1=less sweet than the control solution but still sweet

TABLE 10

| Organoleptic evaluation | | |
|---|---|---|
| Compound | compared to sucrose | compared to mogroside V |
| Ll | 3 | 3 |

Example 3

Formulation Example

The following Tables 11 provides a formulation example for Compound Ll:

TABLE 11

| Hard boiled candy, sugar-free; all amounts in % b.w. | |
|---|---|
| Composition | Amount |
| Isomalt | 94.98 |
| Xylitol | 2.40 |
| Compound Kk | — |
| Compound Ll | 0.01 |
| Compound Mm | — |
| Citric acid | 0.050 |
| Cherry aroma | 0.25 |
| Water | Ad 100 |

What claimed is:

1. A method of sweetening or enhancing sweetening effect of a composition that is administered orally to an individual by adding the sweetener compound of formula (I)

(I)

[Chemical structure of compound of formula (I)]

into the composition to sweeten or enhance the sweetening effect in the composition.

2. The method of claim 1, wherein said sweetener of formula (I) is added in an amount of from about 1 to about 2,000 ppm.

3. The method of claim 1 wherein said composition represents a food composition, an oral composition or a pharmaceutical composition.

4. A method of sweetening or enhancing sweetening effect of a composition that is administered orally to an individual by adding the sweetener compound of formula (II)

(II)

[Chemical structure of compound of formula (II)]

into the composition to sweeten or enhance the sweetening effect in the composition.

5. The method of claim 4, wherein said sweetener of formula (II) is administered in the form an extract, said extract being obtained by the method of aqueous and/or alcoholic extraction of plant materials selected from the group consisting of *Momordica grosvenorii* (*Siraitia grosvenori*).

6. The method of claim 5, wherein said extract further contains at least one of the following compounds:

Compound Aa

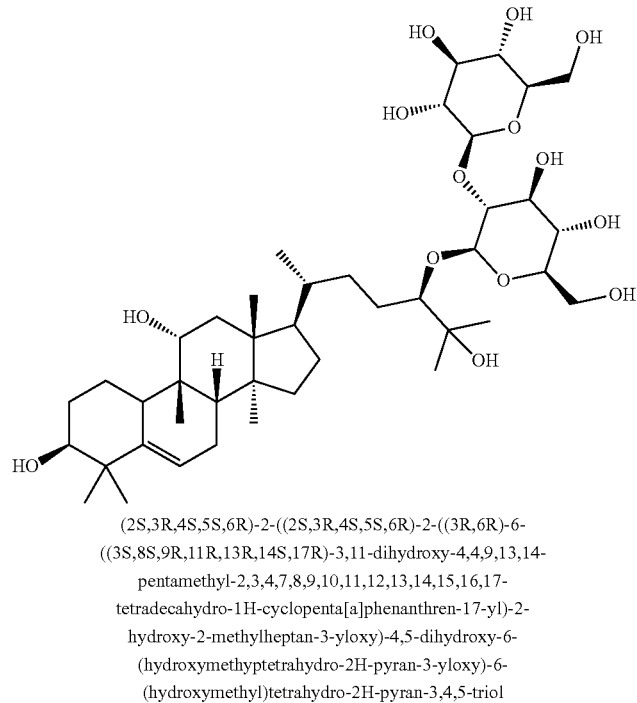

(2S,3R,4S,5S,6R)-2-((2S,3R,4S,5S,6R)-2-((3R,6R)-6-((3S,8S,9R,11R,13R,14S,17R)-3,11-dihydroxy-4,4,9,13,14-pentamethyl-2,3,4,7,8,9,10,11,12,13,14,15,16,17-tetradecahydro-1H-cyclopenta[a]phenanthren-17-yl)-2-hydroxy-2-methylheptan-3-yloxy)-4,5-dihydroxy-6-(hydroxymethyptetrahydro-2H-pyran-3-yloxy)-6-(hydroxymethyl)tetrahydro-2H-pyran-3,4,5-triol Compound Bb

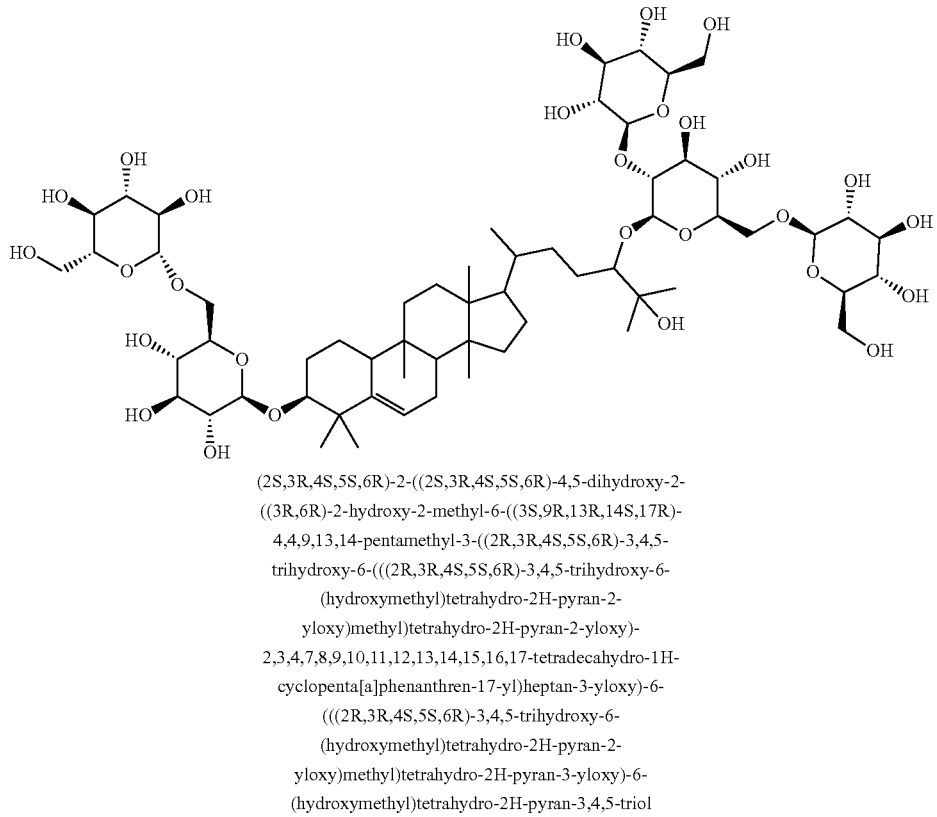

(2S,3R,4S,5S,6R)-2-((2S,3R,4S,5S,6R)-4,5-dihydroxy-2-((3R,6R)-2-hydroxy-2-methyl-6-((3S,9R,13R,14S,17R)-4,4,9,13,14-pentamethyl-3-((2R,3R,4S,5S,6R)-3,4,5-trihydroxy-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol

| Compound Cc |
|---|

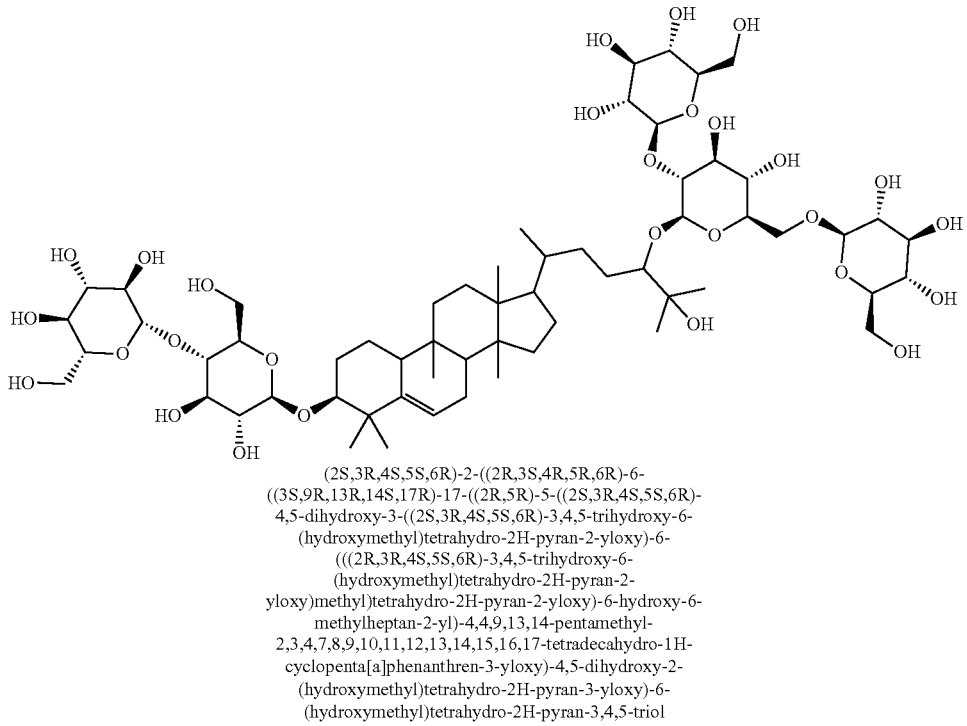

(2S,3R,4S,5S,6R)-2-((2R,3S,4R,5R,6R)-6-
((3S,9R,13R,14S,17R)-17-((2R,5R)-5-((2S,3R,4S,5S,6R)-
4,5-dihydroxy-3-((2S,3R,4S,5S,6R)-3,4,5-trihydroxy-6-
(hydroxymethyl)tetrahydro-2H-pyran-2-yloxy)-6-
(((2R,3R,4S,5S,6R)-3,4,5-trihydroxy-6-
(hydroxymethyl)tetrahydro-2H-pyran-2-
yloxy)methyl)tetrahydro-2H-pyran-2-yloxy)-6-hydroxy-6-
methylheptan-2-yl)-4,4,9,13,14-pentamethyl-
2,3,4,7,8,9,10,11,12,13,14,15,16,17-tetradecahydro-1H-
cyclopenta[a]phenanthren-3-yloxy)-4,5-dihydroxy-2-
(hydroxymethyl)tetrahydro-2H-pyran-3-yloxy)-6-
(hydroxymethyl)tetrahydro-2H-pyran-3,4,5-triol

| Compound Dd |
|---|

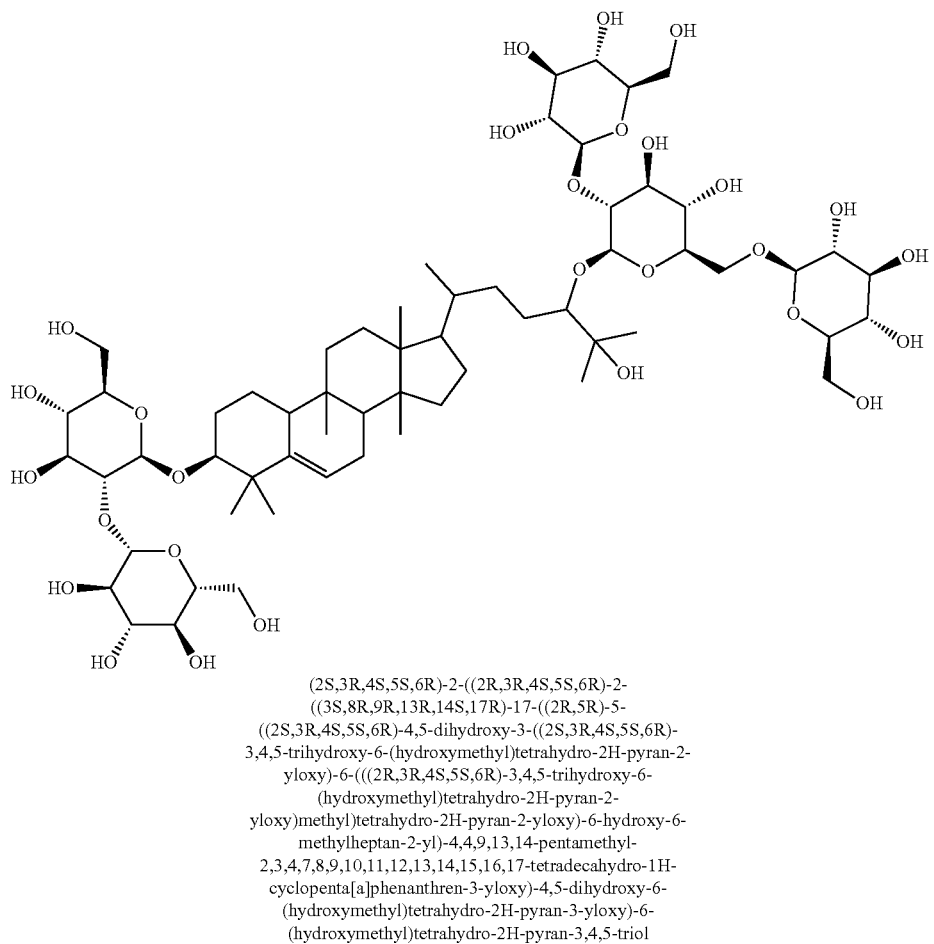

(2S,3R,4S,5S,6R)-2-((2R,3R,4S,5S,6R)-2-
((3S,8R,9R,13R,14S,17R)-17-((2R,5R)-5-
((2S,3R,4S,5S,6R)-4,5-dihydroxy-3-((2S,3R,4S,5S,6R)-
3,4,5-trihydroxy-6-(hydroxymethyl)tetrahydro-2H-pyran-2-
yloxy)-6-(((2R,3R,4S,5S,6R)-3,4,5-trihydroxy-6-
(hydroxymethyl)tetrahydro-2H-pyran-2-
yloxy)methyl)tetrahydro-2H-pyran-2-yloxy)-6-hydroxy-6-
methylheptan-2-yl)-4,4,9,13,14-pentamethyl-
2,3,4,7,8,9,10,11,12,13,14,15,16,17-tetradecahydro-1H-
cyclopenta[a]phenanthren-3-yloxy)-4,5-dihydroxy-6-
(hydroxymethyl)tetrahydro-2H-pyran-3-yloxy)-6-
(hydroxymethyl)tetrahydro-2H-pyran-3,4,5-triol

| Compound Ee | 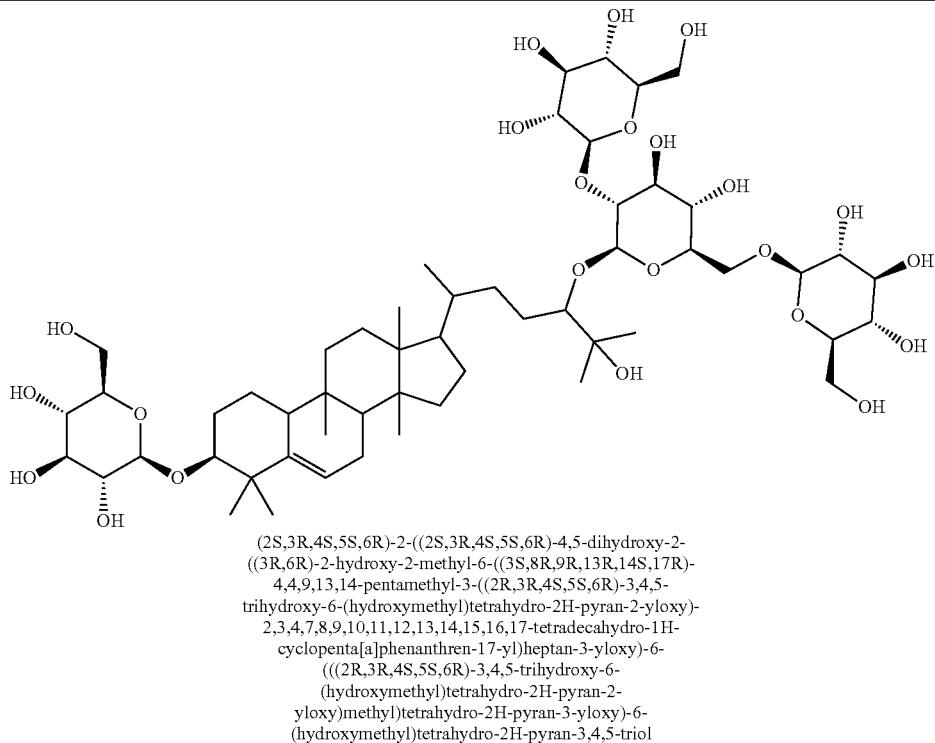 |

(2S,3R,4S,5S,6R)-2-((2S,3R,4S,5S,6R)-4,5-dihydroxy-2-((3R,6R)-2-hydroxy-2-methyl-6-((3S,8R,9R,13R,14S,17R)-4,4,9,13,14-pentamethyl-3-((2R,3R,4S,5S,6R)-3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol

| Compound Ff | 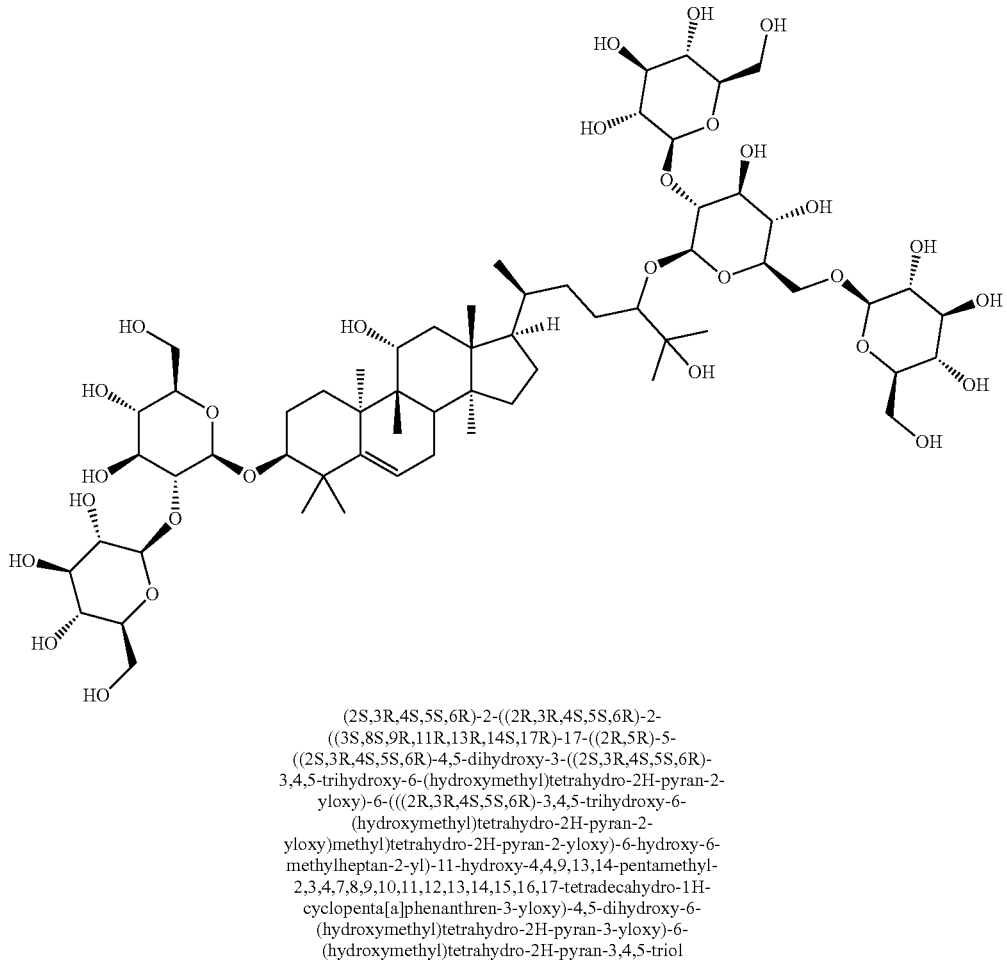 |

(2S,3R,4S,5S,6R)-2-((2R,3R,4S,5S,6R)-2-((3S,8S,9R,11R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-11-hydroxy-4,4,9,13,14-pentamethyl-2,3,4,7,8,9,10,11,12,13,14,15,16,17-tetradecahydro-1H-cyclopenta[a]phenanthren-3-yloxy)-4,5-dihydroxy-6-(hydroxymethyl)tetrahydro-2H-pyran-3-yloxy)-6-(hydroxymethyl)tetrahydro-2H-pyran-3,4,5-triol Compound Gg

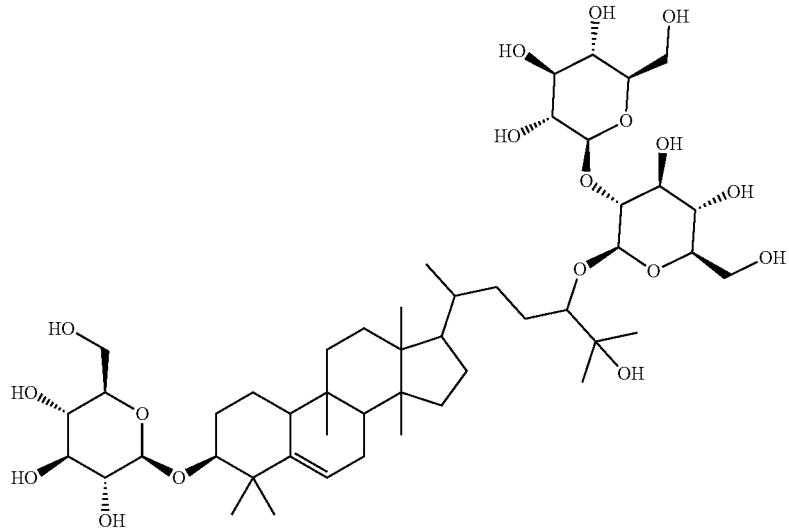

(2S,3R,4S,5S,6R)-2-((2S,3R,4S,5S,6R)-4,5-dihydroxy-2-((3R,6R)-2-hydroxy-2-methyl-6-((3S,9R,13R,14S,17R)-4,4,9,13,14-pentamethyl-3-((2R,3R,4S,5S,6R)-3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-(hydroxymethyl)tetrahydro-2H-pyran-3-yloxy)-6-(hydroxymethyl)tetrahydro-2H-pyran-3,4,5-triol Compound Hh

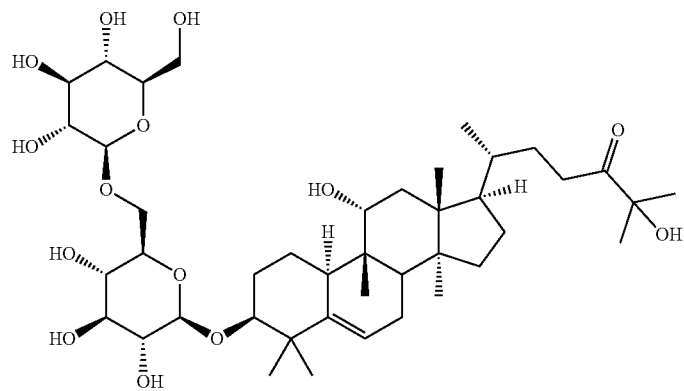

(6R)-2-hydroxy-6-((3S,9R,10R,11R,13R,14S,17R)-11-hydroxy-4,4,9,13,14-pentamethyl-3-((2R,3R,4S,5S,6R)-3,4,5-trihydroxy-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-2,3,4,7,8,9,10,11,12,13,14,15,16,17-tetradecahydro-1H-cyclopenta[a]phenanthren-17-yl)-2-methylheptan-3-one Compound Jj

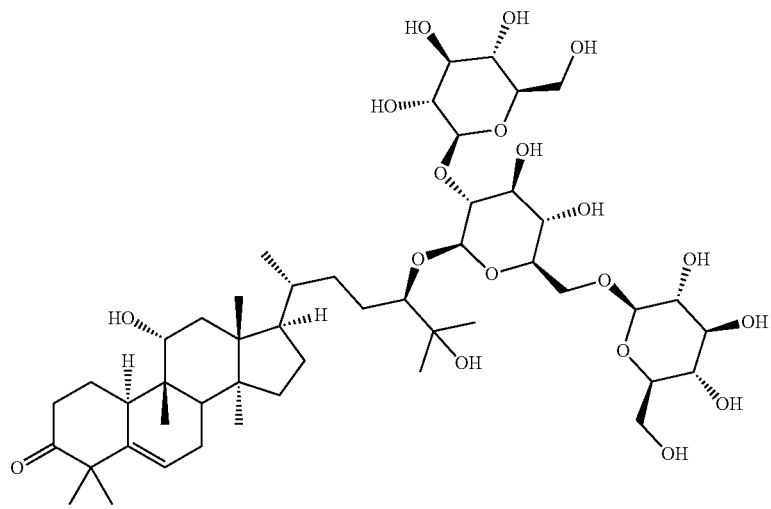

(9R,10R,11R,13R,14S,17R)-17-((2R,5R)-5-
((2S,3R,4S,5S,6R)-4,5-dihydroxy-3-((2S,3R,4S,5S,6R)-
3,4,5-trihydroxy-6-(hydroxymethyl)tetrahydro-2H-pyran-2-
yloxy)-6-(((2R,3R,4S,5S,6R)-3,4,5-trihydroxy-6-
(hydroxymethyl)tetrahydro-2H-pyran-2-
yloxy)methyl)tetrahydro-2H-pyran-2-yloxy)-6-hydroxy-6-
methylheptan-2-yl)-11-hydroxy-4,4,9,13,14-pentamethyl-
4,7,8,9,10,11,12,13,14,15,16,17-dodecahydro-1H-
cyclopenta[a]phenanthren-3(2H)-one Compound Kk

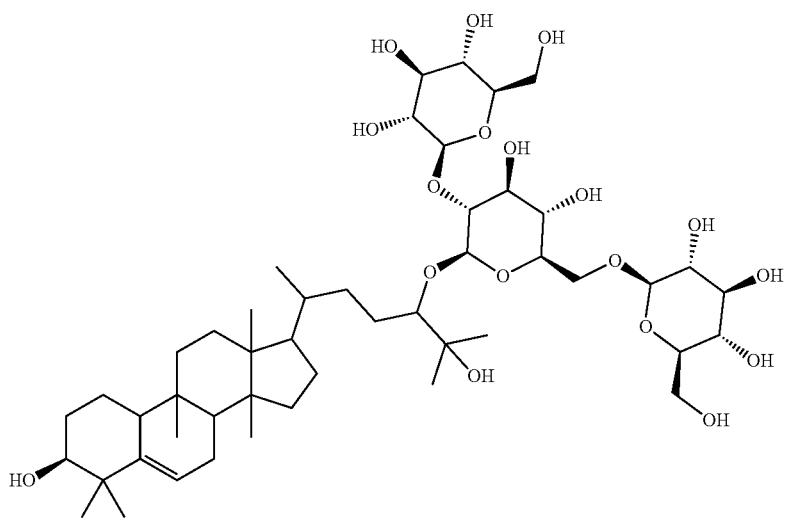

(2S,3R,4S,5S,6R)-2-((2S,3R,4S,5S,6R)-4,5-dihydroxy-2-
((3R,6R)-2-hydroxy-6-((3S,9R,10S,13R,14S,17R)-3-hydroxy-
4,4,9,13,14-pentamethyl-
2,3,4,7,8,9,10,11,12,13,14,15,16,17-tetradecahydro-1H-
cyclopenta[a]phenanthren-17-yl)-2-methylheptan-3-yloxy)-6-
(((2R,3R,4S,5S,6R)-3,4,5-trihydroxy-6-
(hydroxymethyl)tetrahydro-2H-pyran-2-
yloxy)methyl)tetrahydro-2H-pyran-3-yloxy)-6-
(hydroxymethyl)tetrahydro-2H-pyran-3,4,5-triol, or

| Compound Mm | 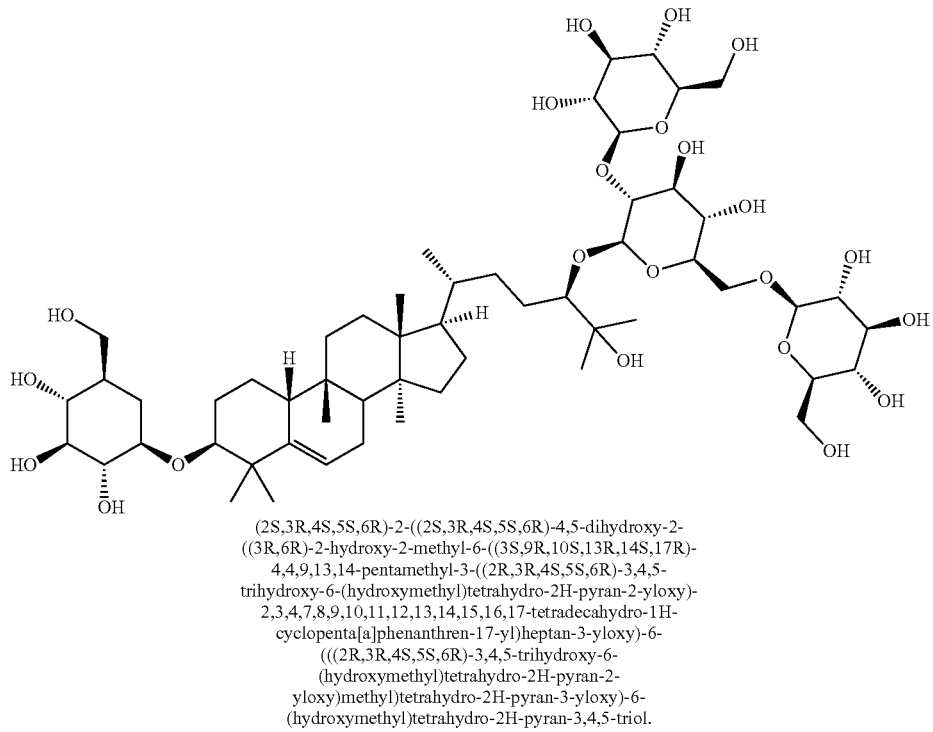<br>(2S,3R,4S,5S,6R)-2-((2S,3R,4S,5S,6R)-4,5-dihydroxy-2-((3R,6R)-2-hydroxy-2-methyl-6-((3S,9R,10S,13R,14S,17R)-4,4,9,13,14-pentamethyl-3-((2R,3R,4S,5S,6R)-3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol. |

7. The method of claim 4, wherein said sweetener of formula (II) is added in an amount of from about 1 to about 2,000 ppm.

8. The method of claim 4, wherein said composition represents a food composition, an oral composition or a pharmaceutical composition.

* * * * *